(12) United States Patent
Alberte et al.

(10) Patent No.: US 7,479,571 B2
(45) Date of Patent: Jan. 20, 2009

(54) GENERATION OF COMBINATORIAL SYNTHETIC LIBRARIES AND SCREENING FOR NOVEL PROADHESINS AND NONADHESINS

(75) Inventors: Randall S. Alberte, Falmouth, ME (US); Robert D. Smith, Falmouth, ME (US)

(73) Assignee: Cernofina, LLC, Fort Meyers, FL (US)

( * ) Notice: Subject to any disclaimer, the term of this patent is extended or adjusted under 35 U.S.C. 154(b) by 0 days.

(21) Appl. No.: 11/052,545

(22) Filed: Feb. 7, 2005

(65) Prior Publication Data

US 2005/0181455 A1  Aug. 18, 2005

Related U.S. Application Data

(63) Continuation of application No. 09/826,287, filed on Apr. 3, 2001, now Pat. No. 7,132,567.

(60) Provisional application No. 60/194,333, filed on Apr. 3, 2000.

(51) Int. Cl.
*C07C 233/65* (2006.01)
*A61K 31/165* (2006.01)

(52) U.S. Cl. .................... 564/158; 558/47; 514/616; 556/465

(58) Field of Classification Search ............. 564/158, 564/153; 514/616; 558/47; 556/465
See application file for complete search history.

(56) References Cited

U.S. PATENT DOCUMENTS

| | | | | |
|---|---|---|---|---|
| 2,179,239 A | * | 11/1939 | Wilmanns et al. | 430/548 |
| 2,635,536 A | * | 4/1953 | Murray | 430/199 |
| 3,022,268 A | * | 2/1962 | Armitage et al. | 524/291 |
| 3,754,031 A | * | 8/1973 | Dexter et al. | 564/158 |
| 3,856,748 A | * | 12/1974 | Dexter et al. | 524/222 |
| 3,869,499 A | | 3/1975 | Heath et al. | |
| 7,132,567 B2 | * | 11/2006 | Alberte et al. | 564/153 |

FOREIGN PATENT DOCUMENTS

| | | | |
|---|---|---|---|
| JP | 53092722 | | 8/1978 |
| JP | 61-14258 | * | 1/1986 |
| JP | 10-175852 | | 6/1998 |

* cited by examiner

*Primary Examiner*—Shailendra Kumar
(74) *Attorney, Agent, or Firm*—Foley Hoag LLP

(57) ABSTRACT

One aspect of the present invention relates to compounds, comprising at least two moieties selected from the group consisting of aryl sulfonates and aryl sulfates. A second aspect of the present invention relates to combinatorial libraries of the aforementioned compounds. The present invention also relates to compositions comprising a compound of the present invention. A fourth aspect of the present invention relates to the use of a compound or composition of the present invention in a method for inhibiting bioadhesion to a surface. Another aspect of the present invention relates to the use of a compound or composition of the present invention in a method for enhancing bioadhesion to a surface.

14 Claims, 3 Drawing Sheets

GENERATION OF COMBINATORIAL SYNTHETIC LIBRARIES AND SCREENING FOR NOVEL PROADHESINS AND NONADHESINS

RELATED APPLICATIONS

This application is a continuation of U.S. patent application Ser. No. 09/826,287, filed Apr. 3, 2001 now U.S. Pat. No. 7,132,567; which claims the benefit of the filing date of and incorporates by reference U.S. Provisional Patent Application Ser. No. 60/194,333, filed Apr. 3, 2000.

BACKGROUND OF THE INVENTION

In nutrient limited ecosystems, bacteria have a marked tendency to adhere to surfaces and initiate the formation of a biofilm. A biofilm is a community of microbes, embedded in an organic polymer matrix, adhering to a surface. In nutrient limited natural and industrial ecosystems biofilm cells will predominate and cause problems as increased frictional resistance to fluids in water conduits and on ship hulls (fouling), decreased heat transfer from heat exchangers, corrosion of metallic substrata and contamination in the food and biotechnology industry. Biofilms are also a severe problem in medical science and industry causing dental plaque, contaminated endoscopes and contact lenses, prosthetic device colonization and biofilm formation on medical implants. More specifically, biofilms cause problems in a variety of areas including the bodies of humans and animals, food processing, health care facilities, metal-working shops, dairy fares and other industries.

Bacteria growing in biofilms are more resistant to antibiotics and disinfectants than planktonic cells and the resistance increases with the age of the biofilm. Bacterial biofilm also exhibits increased physical resistance towards desiccation, extreme temperatures or light. As mentioned, biofilm formation causes industrial, environmental and medical problems and the difficulties in cleaning and disinfection of bacterial biofilm with chemicals is a major concern in many industries. Furthermore, the trend towards milder disinfection and cleaning compositions may increase the insufficient cleaning of surfaces covered with biofilm.

In fact, one of the apparent purposes of natural biofilm formation is for the protection of the constituent microbes from a hostile environment. Consequently, there is a combative interaction between microbes in biofilms and biocidal vehicles such as preservatives, disinfectants and antibiotics. Further, the sessile mode of bacterial growth in biofilms differs from that of the same bacteria species that are present as planktonic cells in a circulating aqueous medium which interfaces with the biofilm. Biofilms also act as a trap for nutrient acquisition, which is an important factor when bacteria grow on surfaces and the nutrient supply is oligotrophic.

Biofilms consist of both host microbes and their extracellular products, usually exopolysaccharides. Microbes have a tendency to form these protective exopolysaccharide matrices after they have adhered to a surface. The formation of biofilm complexes requires only humid conditions and/or water systems and contact with a support surface and/or interface. With respect to nutrients, a nutrient deficiency in fact may increase the biofilm formation capacity of microbes. See 29 *Adv. Appl. Microbiol.* 93 (1983).

In general, biofilms can be produced by almost all microbes under suitable conditions. Various bacteria have been detected in biofilms, including several bacteria having pathogenic potential, such as *Flavobacterium, Moraxella, Achromobacter, Pseudomonas, Alcaligenes, Micrococcus* and *Legionella*. All of these bacteria have the potential to cause infections in humans, and *Legionella*, which is highly resistant to antibiotics, is of particular concern since infection can be fatal. The most common biofilm producers belong to the genera *Pseudomonas, Enterobacter, Flavobacterium, Alcaligenes, Staphylococcus*, and *Bacillus*. There also are anaerobes that can construct corrosive biofilms.

Bacterial deposits on the surfaces of food processing equipment can lead to potential contamination of food products. Bacterial deposits on medical devices such as implants, catheters and intraocular lenses also present the potential for infection when in contact with patients and medical personnel. Consequently, good hygiene standards require that food processing equipment be thoroughly cleaned between uses and that medical and dental equipment be sterilized if possible or at least, for non-surgical instruments, thoroughly cleaned before use. Other surfaces proximate to food processing or medical equipment, such as flooring, walls, tiles, conveyor belts, drains, and packaging, also should be regularly cleaned. Nonetheless, the potential always exists for residual bacterial deposits or for the incidental growth of bacteria on cleaned surfaces, particularly after contact with biological materials as encountered in food processing, e.g., blood, fats, and proteins. For equipment that cannot be thoroughly sterilized between uses, such as most food processing equipment, the potential exists for residual bacteria surface deposits because of the tenacious adherence of bacterial biofilms to the material of the processing equipment, commonly stainless steel but also often including other metals and polymers. Biofilms are communities of microorganisms adhering to surfaces of substrates, usually within a matrix of extracellular polymeric substances. Contamination of biological origin (hereafter biological contamination) on surfaces can include biofilms, blood, proteins, fats, oils, or combinations of such materials.

Besides causing problems in cleaning and hygiene, biofilms can cause energy losses and blockages in condenser and heat exchange tubes, interfere with water and waste water systems, and form drag-inducing encrustations on ship hulls. In the medical disciplines, a biofilm (referred to as "glycocalyx") formed by bacteria such as a *Pseudomonas* species can be the systemic causation of diseases of the lungs or the gastrointestinal and urinary tracts. Additionally, a biofilm formed by bacteria such as *Staphylococcus* species can be a serious contamination problem in foreign-body instruments such as cardiac pacemakers, catheters, prostheses, artificial valves, and the like. Dental plaque is also a typical form of biofilm.

SUMMARY OF THE INVENTION

One aspect of the present invention relates to compounds, comprising at least two moieties selected from the group consisting of aryl sulfonates and aryl sulfates. A second aspect of the present invention relates to combinatorial libraries of the aforementioned compounds. The present invention also relates to compositions comprising a compound of the present invention. A fourth aspect of the present invention relates to the use of a compound or composition of the present invention in a method for inhibiting bioadhesion to a surface.

Another aspect of the present invention relates to the use of a compound or composition of the present invention in a method for enhancing bioadhesion to a surface.

DETAILED DESCRIPTION OF THE INVENTION

Combinatorial libraries of small organic molecules have been synthesized for and screened for their ability to control bioadhesive processes. In part the invention relates to the identification of molecules that inhibit bioadhesion to surfaces (termed "nonadhesins") and molecules that enhance bioadhesion (termed "proadhesins"). Molecules contained within the combinatorial library comprise a sulfooxy ester group. Sulfooxy ester groups have previously been shown to participate directly in bioadhesive control mechanisms.

Figure 1:
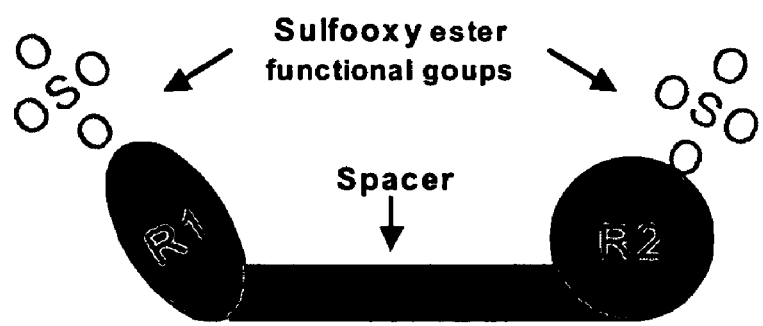
FIG. 1 depicts the basic structure of a compound comprising two sulfooxy ester moieties.

One class of the combinatorial libraries of the present invention consists of molecules containing two sulfooxy ester functional groups linked to a spacer of varying structural lengths or conformations (See FIG. 1). However, the library may contain molecules with only a single sulfooxy ester functional group attached to the spacer. The sulfooxy ester moieties of the compounds of a library may be derived from alcohol building blocks of varying structures (See Scheme 1) that are subsequently sulfonated.

Spacers will provide a site of attachment for functional groups as well as a linkage site to solid supports in order to facilitate solid phase synthesis of the combinatorial libraries. An additional functional role of the spacer is to provide varying distances and orientations between the sulfooxy ester functional groups. It is expected these combinatorial libraries will yield novel molecules that more actively control bioadhesive mechanisms. (See Scheme 2 & FIG. 2).

Scheme 1.
Illustrative examples of alcohol building blocks that can be sulfonated to produce sulfooxy ester functional groups.
Also illustrated are examples of spacer building blocks.

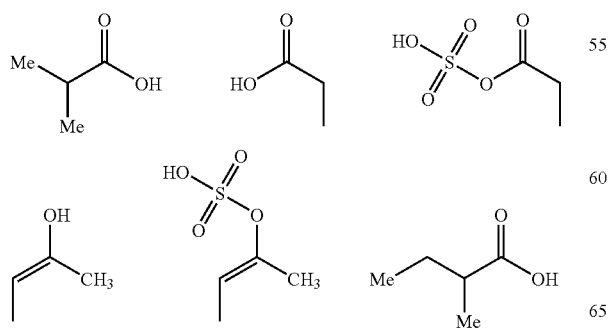

-continued

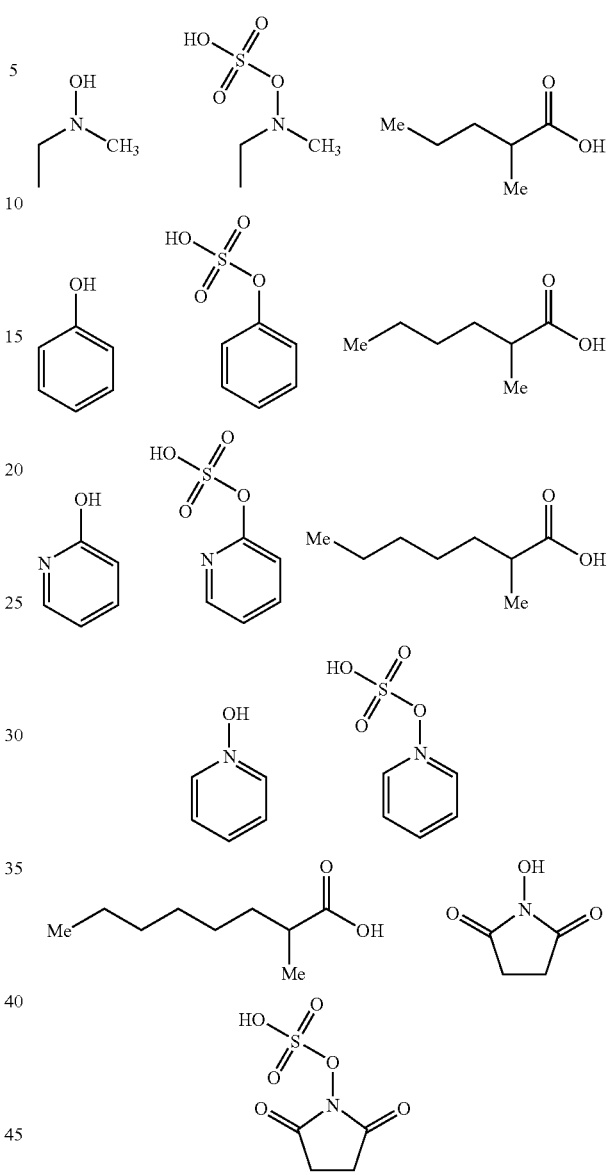

Scheme 2.
Illustrative examples of sulfooxy ester compounds present in a combinatorial library.

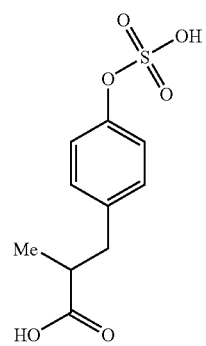

-continued

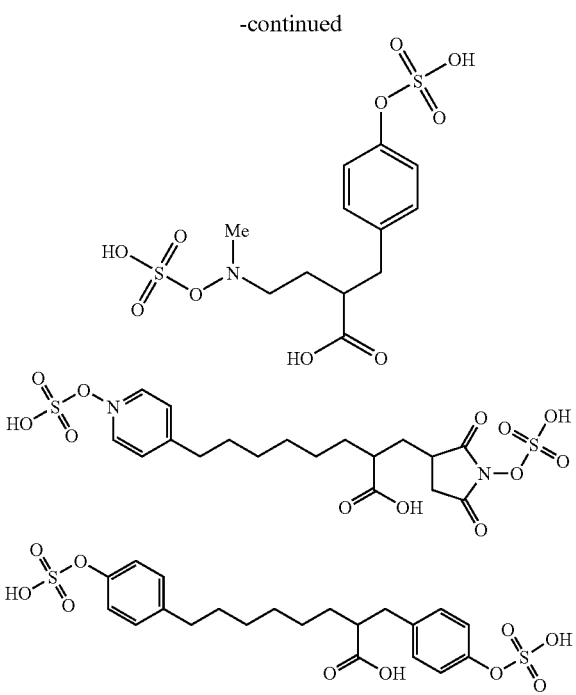

Figure 2:
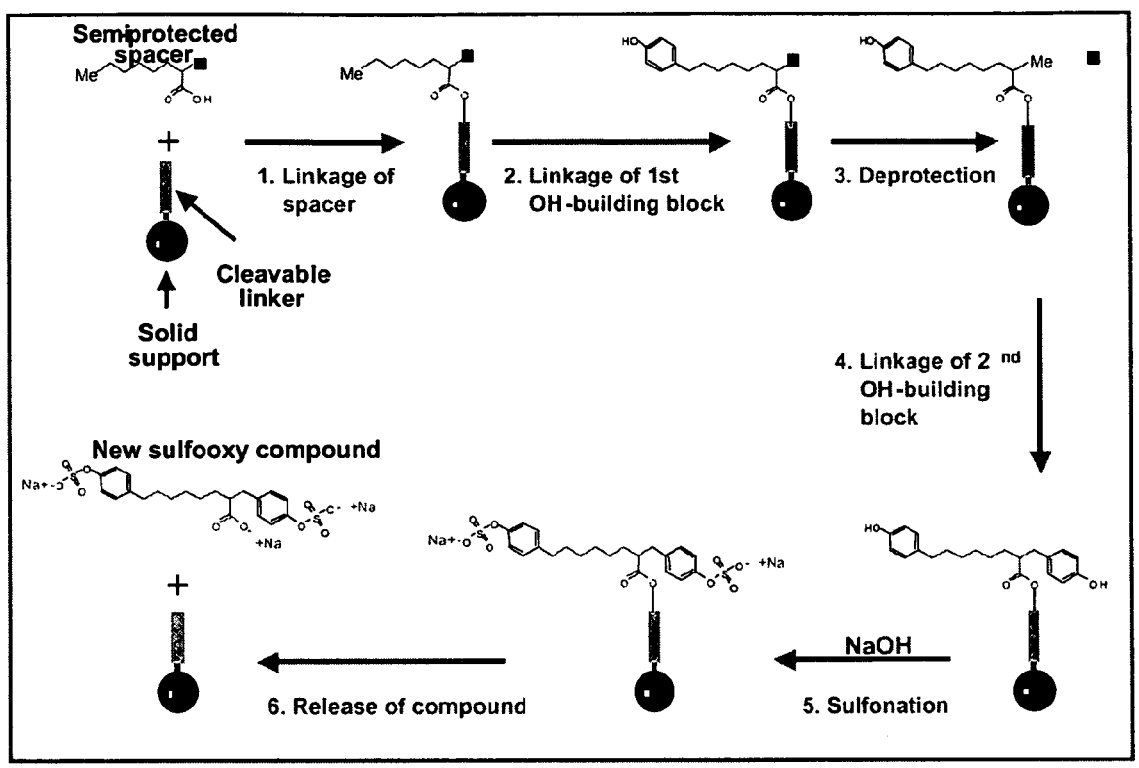
FIG. 2 depicts a strategy for solid phase synthesis of sulfooxy ester compounds.

Certain combinatorial libraries were synthesized on solid supports using a cleavable linker (See, e.g., FIG. 2). This approach allows screening of library compounds in solution (See FIG. 3). Moreover, synthesis of combinatorial libraries in solution has been carried out.

Figure 3:
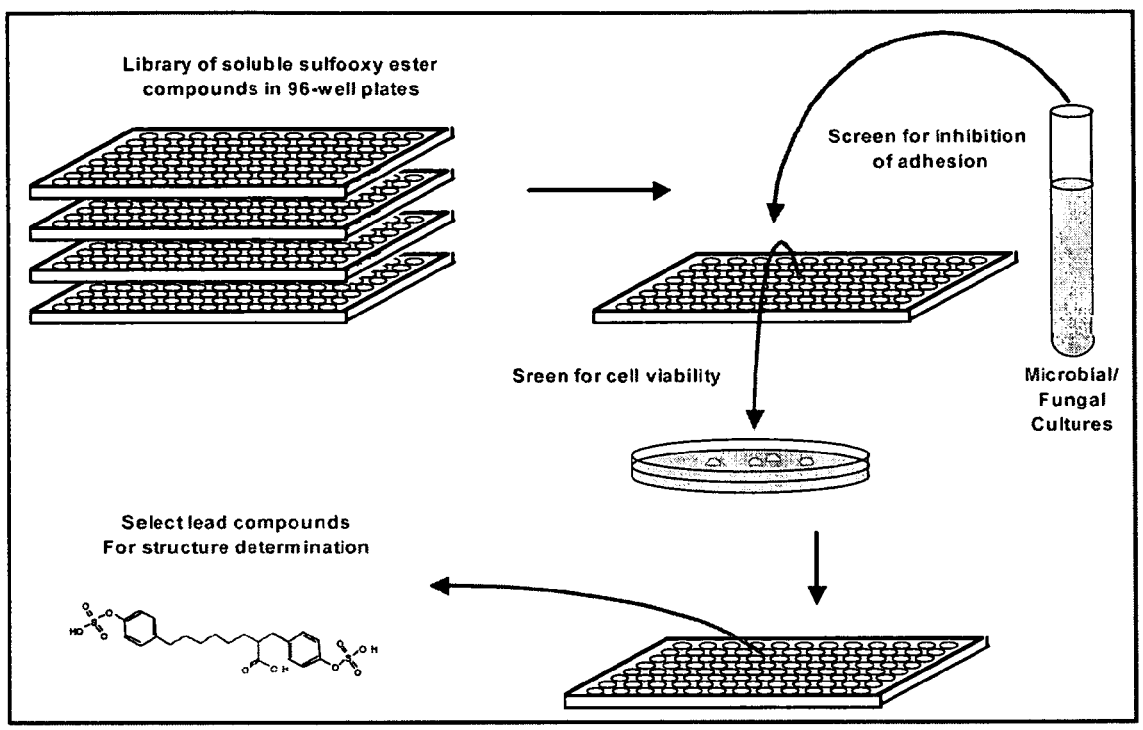
FIG. 3 depicts a strategy for screening combinatorial libraries for novel nonadhesins.

Combinatorial libraries of sulfooxy ester compounds have been screened using a 96-well-based adhesion assay utilizing fluorescence tagging of bacteria or fungal spores. This screen can also be extended to include other organisms including viruses, yeast and invertebrate larvae. A summary of the screening approach is illustrated in FIG. 3. The screening strategy includes both an adhesion and a viability assay in order to identify non-biocidile molecules with adhesion control properties.

Active molecules identified through the above screening methods are then advanced for further characterization. Advancement includes structural determination, solubility properties, efficacy testing against a broad range of hosts, and toxicity evaluations.

DEFINITIONS

For convenience, certain terms employed in the specification, examples, and appended claims are collected here.

The term "surface" as used herein relates to any surface which may be covered by a biofilm layer. Examples of surfaces may be any hard surface such as metal, plastics, rubber, board, glass, wood, paper, concrete, rock, marble, gypsum and ceramic materials which optionally are coated, e.g with paint, enamel etc.; or any soft surface such as fibres of any kind (yarns, textiles, vegetable fibres, rock wool, hair etc.); or porous surfaces; skin (human or animal); keratinous materials (nails etc.). The hard surface can be present in a process equipment member of a cooling tower, a water treatment plant, a dairy, a food processing plant, a chemical or pharmaceutical process plant. The porous surface can be present in a filter, e.g. a membrane filter.

The term "biofilm" refers to an accumulation of organisms on a surface. A mature biofilm can comprise a colony of microorganisms resident upon a surface surrounded by an exopolysaccharide.

"Biofouling organisms" refer to organisms or cells thereof that attach to surfaces and cause or contribute to biofouling or biofilm formation. These organisms can live in a wide range of environments, but most typically are in contact with a liquid or otherwise moist or humid environment. Biofouling organisms can live in either high or low flow aqueous environments, over a broad range of temperatures and pHs. Included are natural and man-made aquatic environments, including salt water, fresh water and brackish water. Also included are semi-aqueous or periodically aqueous environments which expose surfaces to high humidity, precipitation, or periodic flooding. Biofouling organisms can attach to surfaces at various stages of their life cycle, including larval stages, as well as adult. Examples of biofouling organisms include: macrofoulers, such as polychaetes colonial tunicates, and other sessil invertebrates including barnacles, bacteria, (gram negative and gram positive), algae, protists and fuigi.

"Biofilm resistant" or "antifouling" refers to inhibition of attachment and/or growth of a biofouling organism.

A "biofoul or biofilm resistant coating" refers to any coating or surface that inhibits attachment and/or growth of biofouling organisms The term "biologic" as used herein refers to any biofouling organism or any other organism capable of establishing an infection or otherwise causing pathological change in a host organism.

The term "nonadhesin" as used herein refers to any molecule that inhibits adhesion of biologics to surfaces.

The term "proadhesin" as used herein refers to any molecule that enhances adhesion of biologics to surfaces.

The term "aquatic vessel" as used herein refers to any vehicle or container at least part of which is submerged in water or an aqueous solution during its use or storage.

The term "off-shore platform" as used herein refers to any structure floating on the surface of or at least partly immersed in a body of water and secured to the floor of the body of water by legs extending from the structure to the floor.

The term "harbor infrastructure" as used herein refers to facilities provided in a port. Such facilities include, for example, docks, mooring poles, anchorage points, and other facilities known to one of ordinary skill in the art.

The term "conduit" as used herein refers to any channel through which a fluid is conveyed, said channel may comprise a filter. Such channels include, for example, a pipe, a tube, a hose, a faucet, a water storage device such as a water tower, and any other channel known to one of ordinary skill in the art.

The term "cable" as used herein refers to any assembly of fiber strands, wire, or metal links twisted or braided together or around a core, or any assemble of electrical conductors insulated from each other but laid up together usually by being twisted around a central core, or any other structure known to one of ordinary skill in the art.

The term "laboratory apparatus" as used herein refers to any structure, device, or article that may be used in a laboratory, especially any structure, device, or article that may be exposed to or submerged at least partly in water or an aqueous solution during its use or storage. Examples of such apparatus include water baths, glassware, plasticware, heating elements, incubators, and any other structures, devices, and articless known to one of ordinary skill in the art.

The term "virion" as used herein refers to any complete virus particle that consists of an RNA or DNA core with a protein coat and optionally with at least one external envelope.

The term "virion protein coat" as used herein refers to any capsid.

The term "virion envelope" as used herein refers to any external membrane of a virion and comprises a phospholipid bilayer and optionally at least one glycoprotein.

The term "implantable medical device" as used herein refers to any device that may be placed within the confines of an organism, either temporarily or permanently. Examples of implantable medical devices include pins, screws, plates, artificial joints and components thereof, artificial limbs and prostheses, sutures, shunts, artificial heart valves, artificial pacemakers and defibrillators, infusion pumps, vascular graft prostheses, tissue expanders, any other device known to one of ordinary skill in the art.

The term "insertable medical device" as used herein refers to any device that may be applied to the surface of an organism or placed partially inside an organism through a naturally existing or artificially created site of entry. Examples of such devices include contact lenses, stoma appliances, an artificial larynx, endotracheal tube, nasogastric tube, gastrostomy tube, jejunostomy tibe, ileostomy tube, tracheostomy tube, intravenous catheter, Hickman catheters, vascular access device, transhepatic catheters, biliary drainage tube, urinary catheter, dialysis catheter, tympanostomy tubes, and any other devices known to one of ordinary skill in the art.

The term "food processing surface" as used herein refers to any surface used in the isolation, washing, cleaning, draining, manufacture, preparation, mixing, blending, serving, disposal, or storage of any material provided for, intended for, or being evaluated for digestive consumption by a human or non-human animal, or in any other step of food processing known to one of ordinary skill in the art. Example of such surfaces include tables, countertops, blenders, mixers, food processors, mixing bowls, serving bowls, sinks, wastebaskets, surfaces inside refrigerators and freezers, any utensils coming in contact with the material prepared, and any other surfaces recognized by one of ordinary skill in the art.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251-259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The terms "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; and the term "hydroxyl" means —OH.

The terms "amine" and "amino" are art-recognized and refer to both unsubstituted and substituted amines, e.g., a moiety that can be represented by the general formula:

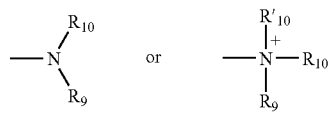

wherein $R_9$, $R_{10}$ and $R'_{10}$ each independently represent a group permitted by the rules of valence.

The term "acylamino" is art-recognized and refers to a moiety that can be represented by the general formula:

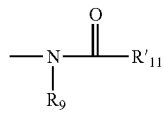

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

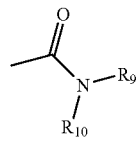

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

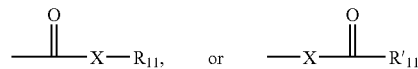

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}$' is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

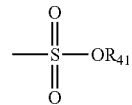

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

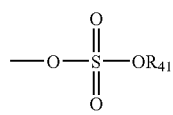

in which $R_{41}$ is as defined above.

The term "sulfonylamino" is art recognized and includes a moiety that can be represented by the general formula:

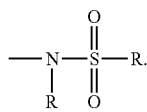

The term "sulfamoyl" is art-recognized and includes a moiety that can be represented by the general formula:

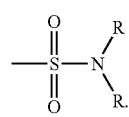

The term "sulfonyl", as used herein, refers to a moiety that can be represented by the general formula:

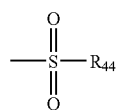

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

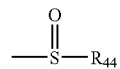

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as inhibitors of leukotriene activity or histamine activity), wherein one or more simple variations of substituents are made which do not adversely affect the efficacy of the compound in inhibiting the above activities. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

Compounds and Methods of the Invention

In certain embodiments, the present invention relates to a compound represented by 1:

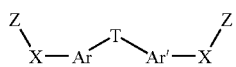

wherein

X represents independently for each occurrence a bond, O, S, or NR';

Z represents independently for each occurrence H, acyl, trialkylsilyl, alkylsulfonyl, fluoroalkylsulfonyl, arylsulfonyl, or $S(O)_2OH$;

Ar and Ar' are independently selected from the group consisting of optionally substituted aryl and heteroaryl;

T represents a covalent tether connecting Ar and Ar', wherein said covalent linker comprises an amide, ether, amine or ester moiety;

R represents independently for each occurrence H, alkyl, aryl, or aralkyl;

R' represents independently for each occurrence H, alkyl, alkenyl, aryl, aralkyl, formyl, acyl, sulfonyl, or $-(CH_2)_m-R_{80}$;

$R_{80}$ represents independently for each occurrence aryl, cycloalkyl, cycloalkenyl, or heterocyclyl; and m is an integer in the range 0 to 8 inclusive.

In certain embodiments, a compound of the present invention is represented by 1 and the attendant definitions, wherein X represents independently for each occurrence a bond or O.

In certain embodiments, a compound of the present invention is represented by 1 and the attendant definitions, wherein X represents O.

In certain embodiments, a compound of the present invention is represented by 1 and the attendant definitions, wherein Z represents independently for each occurrence alkylsulfonyl, fluoroalkylsulfonyl, arylsulfonyl, or $S(O)_2OH$.

In certain embodiments, a compound of the present invention is represented by 1 and the attendant definitions, wherein Z represents independently for each occurrence methylsulfonyl, trifluoromethylsulfonyl, or $S(O)_2OH$.

In certain embodiments, a compound of the present invention is represented by 1 and the attendant definitions, wherein Ar and Ar' represent independently for each occurrence optionally substituted aryl.

In certain embodiments, a compound of the present invention is represented by 1 and the attendant definitions, wherein Ar and Ar' represent independently for each occurrence optionally substituted phenyl or naphthyl.

In certain embodiments, a compound of the present invention is represented by 1 and the attendant definitions, wherein X represents O; and Z represents independently for each occurrence alkylsulfonyl, fluoroalkylsulfonyl, arylsulfonyl, or $S(O)_2OH$.

In certain embodiments, a compound of the present invention is represented by 1 and the attendant definitions, wherein X represents O; and Z represents independently for each occurrence methylsulfonyl, trifluoromethylsulfonyl, or $S(O)_2OH$.

In certain embodiments, a compound of the present invention is represented by 1 and the attendant definitions, wherein X represents O; Z represents independently for each occurrence alkylsulfonyl, fluoroalkylsulfonyl, arylsulfonyl, or $S(O)_2OH$; and Ar and Ar' represent independently for each occurrence optionally substituted aryl.

In certain embodiments, a compound of the present invention is represented by 1 and the attendant definitions, wherein X represents O; Z represents independently for each occurrence methylsulfonyl, trifluoromethylsulfonyl, or $S(O)_2OH$; and Ar and Ar' represent independently for each occurrence optionally substituted aryl.

In certain embodiments, a compound of the present invention is represented by 1 and the attendant definitions, wherein X represents O; Z represents independently for each occurrence alkylsulfonyl, fluoroalkylsulfonyl, arylsulfonyl, or $S(O)_2OH$; and Ar and Ar' represent independently for each occurrence optionally substituted phenyl or naphthyl.

In certain embodiments, a compound of the present invention is represented by 1 and the attendant definitions, wherein X represents O; Z represents independently for each occurrence methylsulfonyl, trifluoromethylsulfonyl, or $S(O)_2OH$; and Ar and Ar' represent independently for each occurrence optionally substituted phenyl or naphthyl.

In certain embodiments, a compound of the present invention is represented by 1 and the attendant definitions, wherein T represents $-C(O)NR-Q-NRC(O)-$; Q is $-(CH_2)_n-$ or heterocyclyl; and n is an integer selected from the range 2 to 10 inclusive.

In certain embodiments, a compound of the present invention is represented by 1 and the attendant definitions, wherein T represents $-(CH_2)-NR-Q-O-$; and Q represents alkyl, cycloalkyl, or heterocyclyl.

In certain embodiments, a compound of the present invention is represented by 1 and the attendant definitions, wherein T represents —(CH$_2$)—NR—Q—O—C(O)— or —(CH$_2$)—NR—Q—O—C(O)—(CH=CH)—; and Q represents alkyl, cycloalkyl, or heterocyclyl.

In certain embodiments, a compound of the present invention is represented by 1 and the attendant definitions, wherein T represents —(CH$_2$)—NR—Q—; and Q is a bond, alkyl, or heterocyclyl.

In certain embodiments, a compound of the present invention is represented by 1 and the attendant definitions, wherein T represents —CH$_2$CH(C(O)NHMe)—NRC(O)—Q—C(O)NR—G—; Q is alkyl, cycloalkyl, cycloalkenyl, heterocyclyl, alkenyl, aryl, heteroaryl, aralkyl, alkyl-O-alkyl, or alkyl-S-alkyl; and G is a bond, alkyl, or heterocyclyl.

In certain embodiments, the present invention relates to a combinatorial library consisting of a plurality of compounds of the present invention.

In certain embodiments, the present invention relates to a method of inhibiting the adhesion to a surface by a bacterium, fungus, virion, freshwater invertebrate, or marine invertebrate, comprising the step of treating a surface with an effective amount of a compound of the present invention. In certain embodiments, said surface is a portion of an exterior surface of an aquatic vessel. In certain embodiments, said surface is a portion of an exterior surface of an off-shore platform. In certain embodiments, said surface is a portion of an exterior surface of a harbor infrastructure. In certain embodiments, said surface is a portion of an exterior or interior surface of a conduit for water or an aqueous solution. In certain embodiments, said surface is a portion of an exterior surface of a cable. In certain embodiments, said surface is a portion of an exterior or interior surface of a laboratory apparatus. In certain embodiments, said surface is a portion of an animal cell membrane. In certain embodiments, said surface is a portion of a mammalian cell membrane. In certain embodiments, said surface is a portion of a human cell membrane. In certain embodiments, said surface is a portion of an exterior surface of a plant. In certain embodiments, said surface is a portion of an exterior surface of a plant component. In certain embodiments, said surface is a portion of the cell membrane of a fungus. In certain embodiments, said surface is a portion of the cell wall of a fungus. In certain embodiments, said surface is a portion of the cell membrane of a bacterium. In certain embodiments, said surface is a portion of the cell wall of a bacterium. In certain embodiments, said surface is a portion of a virion protein coat. In certain embodiments, said surface is a portion of a virion envelope. In certain embodiments, said surface is a portion of an exterior surface of an implantable medical device. In certain embodiments, said surface is a portion of an exterior surface of an insertable medical device. In certain embodiments, said surface is a portion of a food processing surface.

In certain embodiments, the present invention relates to a method of enhancing the adhesion to a surface by a bacterium, fungus, virion, freshwater invertebrate, or marine invertebrate, comprising the step of treating a surface with an effective amount of a compound of the present invention. In certain embodiments, said surface is a portion of an exterior surface of an aquatic vessel. In certain embodiments, said surface is a portion of an exterior surface of an off-shore platform. In certain embodiments, said surface is a portion of an exterior surface of a harbor infrastructure. In certain embodiments, said surface is a portion of an exterior or interior surface of a conduit for water or an aqueous solution. In certain embodiments, said surface is a portion of an exterior surface of a cable. In certain embodiments, said surface is a portion of an exterior or interior surface of a laboratory apparatus. In certain embodiments, said surface is a portion of an animal cell membrane. In certain embodiments, said surface is a portion of a mammalian cell membrane. In certain embodiments, said surface is a portion of a human cell membrane. In certain embodiments, said surface is a portion of an exterior surface of a plant. In certain embodiments, said surface is a portion of an exterior surface of a plant component. In certain embodiments, said surface is a portion of the cell membrane of a fungus. In certain embodiments, said surface is a portion of the cell wall of a fungus. In certain embodiments, said surface is a portion of the cell membrane of a bacterium. In certain embodiments, said surface is a portion of the cell wall of a bacterium. In certain embodiments, said surface is a portion of a virion protein coat. In certain embodiments, said surface is a portion of a virion envelope. In certain embodiments, said surface is a portion of an exterior surface of an implantable medical device. In certain embodiments, said surface is a portion of an exterior surface of an insertable medical device. In certain embodiments, said surface is a portion of a food processing surface.

Commercial Applications

Disclosed herein are compounds, and combinatorial libraries thereof, for use on surfaces susceptible to adhesion by various biologics. Such "antifouling" substances may be employed to prevent damage by biologics to such surfaces, prevent formation of biofilms on such surfaces, prevent infection by biologics of such surfaces, suppress thrombogenic properties of such surfaces, and other uses readily apparent to those skilled in the appropriate arts. Examples of biologics include, but are not limited to, bacteria, fungi, viruses, protozoans, and marine invertebrates.

In certain embodiments, compounds of the invention may prevent fouling by biologics of surfaces in prolonged contact with aqueous environments. Examples of such surfaces include, but are not limited to, hulls of ships immersed in sea- or fresh water, laboratory equipment immersed in water-filled incubators, and water conduits, such as pipes or vaporization apparatus immersed in water reservoirs of air humidifiers. In certain embodiments, these compounds may prevent fouling by algae, barnacles, barnacle larvae, diatoms, mussels, and other marine- and fresh-water organisms known to one of ordinary skill in the art.

In certain embodiments, these compounds affect the agglutination of bacterial and mammalian cells. The effects of these compounds on cell agglutination may involve the blocking of certain cell surface receptors and the activation of others, such as those involved in the attachment to extracellular surfaces and which thereby mediate fouling. Thus, these compounds may possess many of the activities of naturally-occurring proteins and glycoproteins which bind to sites on the surface of a cell and thereby affect cell/cell interactions.

The instant claimed compounds interfere with the attachment of organisms to surfaces, thereby having broad applicability in effectively inhibiting the attachment of a variety of organisms. In addition, the compounds are relatively safe for wide-spread environmental use, as they naturally degrade into carbon dioxide and water, or simple organic acids.

In certain embodiments, compounds have a relatively short half-life after release, rendering them particularly well-suited for widespread environmental use. In certain embodiments, compounds can be readily synthesized.

In certain embodiments, compounds of the instant invention may prevent infection of plants and plant components by plant pathogens. "Plant component" refers to a portion or part of a plant. Examples include: seeds, roots, stems, vascular systems, fruits (further including pip fruits (e.g. apples, pears, quinces)), citrus fruits (oranges, lemons, limes, grapefruits, mandarins, nectarines), stone fruits (peaches apricots, plums, cherries, avocados, grapes), berries (strawberries, blueberries, raspberries, blackberries)), leaves, grains and vegetables.

A "plant pathogen" refers to an organism (bacteria, virus, protist, algae or fungi) that infects plants of plant components. Examples include molds, fungi and rot that typical use spores to infect plants or plant components (e.g fruits, vegetables, grains, stems, roots). Spores must recognize the host, attach, germinate, penetrate host tissues, and proliferate hyphae that will allow the fungus access to nutrients for growth and reproduction. Examples include: *Botrytis* sp. (*B. cinerea*), *Penicillium* sp. (*P. expansum, P. italicum, P. digitalum*), *Rhizopus* sp. (*R. sulonifer, R. nigricans*), *Alternaria* sp. (*A. alternata, A. solani*), *Diploidia* sp. (*D. natalenses*), *Monilinia* sp. (*M. fructicola*), *Pseudomonas* sp. (*P. cepacia*), *Xanthomonas* sp., *Erwinia* sp., *Corynebacterium* sp., *Cladosporium* sp. (*C. fulva*), *Phytophtora* sp. (*P. infestans*), *Colletotricum* sp. (*C. coccoides C. fragariae, C. gloesporioides*), *Fusarium* sp. (*F. lycopersici*), *Verticillium* sp. (*V. alboatrum, V dahliae*), *Unicula* sp. (*U. necator*), *Plasmopara* sp. (*P. viticola*), *Guignardia* sp. (*G. bidwellii*), *Cercospora* sp. (*C. arachidicola*), *Scelrotinia* sp. (*S. scerotiorum*), *Puccinia* sp. (*P. arachidis*), *Aspergillus* sp. (*A. flavus*), *Venturia* sp. (*V. inaequalis*) *Podosphaera* sp. (*P. leucotricha*), *Pythiun* sp., *Sphaerotheca* sp. (*S. macularis*), and *Bacillus* sp. (*B. subitlis*).

In certain embodiments, compounds of the invention may provide one or more plant and animal lectin-like activities. Lectins bind to cell surface proteoglycans, which function in the attachment of pathogens such as viruses and bacteria. Accordingly the lectin-like activities of compounds of the invention are useful in treating and preventing infections and other receptor-mediated diseases and conditions.

The ability of the compounds to bind to certain cell surface sites is useful for agonizing or antagonizing certain cell surface interactions which are otherwise affected by animal or plant lectin proteins. The extracellular polysaccharides produced by fouling organisms are often highly sulfated, and these sulfate esters play an important role in polymerization (e.g. glue/gel formation).

In certain embodiments, compounds of the invention may prevent infection of humans by human pathogens, including but not limited to bacteria, viruses, protozoans, parasites, and fungi. Infection may be prevented by inhibiting adhesion of such pathogens to cell membranes and tissue surfaces in humans. In certain embodiments, compounds of the invention may similarly prevent infection of mammals and other animals by biologics.

In certain embodiments, compounds of the invention may inhibit attachment of parasitic fingi spores to plants, as well as hyphal production from previously attached spores. Even after prolonged exposure, the presence of the compounds of the invention on the plants did not result in any toxic or growth inhibitory effect.

By blocking spore attachment, an initial step in the infection process, the compounds of the invention may provide a highly effective antifungal and antibacterial agent. In addition, the compounds of the present invention are also capable of interfering with the attachment, germination, penetration by fungal plant pathogens. Further, because essentially all fungal plant pathogens use spores to recognize the host plant, attach, germinate, penetrate the host plant tissue and proliferate hyphae that allows the fungus access to the plant's nutrients for growth and reproduction, the compounds are broad-based antifungal agents. In addition a series of investigations on several species of bacteria, microalgae, macroalgal spores and invertebrates has confirmed that the inhibitory mode-of-action is through a non-toxic means (Zimmerman et al., (1995) U.S. Pat. No. 5,384,176; Zimmerman et al., (1997) U.S. Pat. No. 5,607,741; Todd et al., *Phytochemistry* 34: 401-404 (1993); Sundberg et al., *Naval Research Reviews* (1997) 4: 51-59).

The compounds of the invention can also be used to inhibit or to destroy the microorganisms occurring on plants or on parts of plants (the fruit, blossom, leaves, stems, tubers or roots) of various crops of useful plants, while at the same time parts of plants that grow later are also protected against such microorganisms. They can also be used as dressings in the treatment of plant propagation material, especially seed (fruit, tubers, grains) and plant cuttings (for example rice), to provide protection against fungal infections and against phytopathogenic fungi occurring in the soil. The compound mixtures according to the invention are distinguished by the fact that they are especially well tolerated by plants and are environmentally friendly.

Target crops to be protected within the scope of the present invention comprise, for example, the following species of plants: cereals (wheat, barley, rye, oats, rice, sorghum and related species); beets (sugar beet and fodder beet); pomes, stone fruit and soft fruit (apples, pears, plums, peaches, almonds, cherries, strawberries, raspberries and blackberries); leguminous plants (beans, lentils, peas and soybeans); oil plants (rape, mustard, poppy, olives, sunflowers, coconut, castor oil plants, cocoa beans and groundnuts); cucumber plants (marrows, cucumber and melons); fiber plants: (cotton, flax, hemp and jute); citrus fruit (oranges, lemons, grapefruit and mandarins); vegetables (spinach, lettuce, asparagus, cabbages, carrots, onions, tomatoes, potatoes and paprika); lauraceae (avocados, cinnamon and camphor); or plants such as maize, tobacco, nuts, coffee, sugar cane, tea, vines, hops, bananas and natural rubber plants, as well as ornamental plants (flowers, shrubs, broad-leaved trees and evergreens, such as conifers).

One of skill in the art will recognize that the composition of the invention can be varied as required to optimize the overall chemical properties of the particular compound for specific uses, while retaining the antifouling (AF) activity. For example, the length of an alkyl chain can be extended or shortened to control the rate of dissolution of the compound from a structure or a coating. Alternatively, additional functional groups can be added to the alkyl chain to further vary the chemical nature of the molecule.

Implantable medical devices, using artificial materials alone or in combination with naturally-derived materials, can be treated with compounds either by surface coating or by incorporation. Metals may be suitably treated with surface coats while retaining their biological properties. In certain embodiments of the present invention, metals may be treated with paints or with adherent layers of polymers or ceramics that incorporate the compounds of the invention. Certain embodiments treated in this manner may be suitable for orthopedic applications, for example, pins, screws, plates or parts of artificial joints. Methods for surface treatment of metals for biological use are well-known in the relevant arts. Other materials besides metals can be treated with surface coats of compounds according to the present invention as the medical application requires.

Implantable devices may comprise materials suitable for the incorporation of the instant claimed compounds. Embodiments whose components incorporate compounds of the invention can include polymers, ceramics and other substances. Materials fabricated from artificial materials can also be destined for resorption when they are placed in the body.

Such materials can be called bioabsorbable. As an example, polyglycolic acid polymers can be used to fabricate sutures and orthopedic devices. Those of ordinary skill in these arts will be familiar with techniques for incorporating agents into the polymers used to shape formed articles for medical applications. AF agents can also be incorporated into glues, cements or adhesives, or in other materials used to fix structures within the body or to adhere implants to a body structure. Examples include polymethylmethacrylate and its related compounds, used for the affixation of orthopedic and dental prostheses within the body. The presence of the compounds of the instant invention can decrease biofilm formation in those structures in contact with the glue, cement, or adhesive. Alternatively, a compound of the invention can coat or can permeate the formed article. In these compositions, the formed article allows diffusion of the compound, or functional portion thereof, into the surrounding environment, thereby preventing fouling of the appliance itself. Microcapsules bearing compounds can also be imbedded in the material. Materials incorporating compounds are adaptable to the manufacture of a wide range of medical devices, some of which are disclosed below. Other examples will be readily apparent to those practitioners of ordinary skill in the art.

In one embodiment, compounds of the invention can be applied to or incorporated in certain medical devices that are intended to be left in position permanently to replace or restore vital functions. As one example, ventriculoatrial or ventriculoperitoneal shunts are devised to prevent cerebrospinal fluid from collecting in the brain of patients whose normal drainage channels are impaired. As long as the shunt functions, fluid is prevented from accumulating in the brain and normal brain function can continue. If the shunt ceases to function, fluid accumulates and compresses the brain, with potentially life-threatening effect. If the shunt becomes infected, it causes an infection to enter the central portions of the brain, another life-threatening complication. These shunts commonly include a silicone elastomer or another polymer as part of their fabrication. Silicones are understood to be especially suited for combination with compounds according to the present invention.

Another shunt that has life-saving import is a dialysis shunt, a piece of polymeric tubing connecting an artery and a vein in the forearm to provide the kidney failure patient a means by which the dialysis equipment can cleanse the bloodstream. Even though this is a high-flow conduit, it is susceptible to the formation of biofilms and subsequent infection. If a shunt becomes infected, it requires removal and replacement. Since dialysis may be a lifelong process, and since there are a limited number of sites where shunts can be applied, it is desirable to avoid having to remove one through infectious complications. Imbedding or otherwise contacting the compounds of the invention with the shunt material can have this desired effect.

Heart valves comprising artificial material are understood to be vulnerable to the dangerous complication of prosthetic valve endocarditis. Once established, it carries a mortality rate as high as 70%. Biofilms are integrally involved in the development of this condition. At present, the only treatment for established contamination is high-dose antibiotic therapy and surgical removal of the device. The contaminated valve must be immediately replaced, since the heart cannot function without it. Because the new valve is being inserted in a recently contaminated area, it is common for prosthetic valve endocarditis to affect the replacement valve as well. Artificial heart valves comprised of the compounds of the invention may reduce the incidence of primary and recurrent prosthetic valve endocarditis. Compounds of the invention can be applied to the synthetic portions or the naturally-derived portions of heart valves.

Pacemakers and artificial implantable defibrillators commonly comprise metallic parts in combination with other synthetic materials. These devices, which may be coated with a polymeric substance such as silicone are typically implanted in subcutaneous or intramuscular locations with wires or other electrical devices extending intrathoracically or intravascularly. If the device becomes colonized with microorganisms and infected, it must be removed. A new device can be replaced in a different location, although there are a finite number of appropriate implantation sites on the body. Devices comprising the compounds of the invention may inhibit contamination and infection, or substantially reduce the risk thereof.

Devices implanted into the body either temporarily or permanently to pump pharmacological agents into the body can comprise metallic parts in combination with other synthetic materials. Such devices, termed infusion pumps, can be entirely implanted or can be partially implanted. The device may be partially or entirely covered with a polymeric substance, and may comprise other polymers used as conduits or tubes. Incorporating AF agents according to the present invention into the coating materials imposed upon these devices or into the materials used for the devices themselves, their conduits or their tubing may inhibit their contamination and infection.

Equally lifesaving are the various vascular grafting prostheses and stents intended to bypass blocked arteries or substitute for damaged arteries. Vascular grafting prostheses, made of Teflon, dacron, Gore-tex®, expanded polytetrafluoroethylene (e-PTFE), and related materials, are available for use on any major blood vessel in the body. Commonly, for example, vascular grafting prostheses are used to bypass vessels in the leg and are used to substitute for a damaged aorta. They are put in place by being sewn into the end or the side of a normal blood vessel upstream and downstream of the area to be bypassed or replaced, so that blood flows from a normal area into the vascular grafting prosthesis to be delivered to other normal blood vessels. Stents comprising metallic frames covered with vascular grafting prosthesis fabric are also available for endovascular application, to repair damaged blood vessels.

When a vascular grafting prosthesis becomes infected, it can spread infection through the entire bloodstream. Furthermore, the infection can weaken the attachment of the vascular grafting prosthesis to the normal blood vessel upstream or downstream, so that blood can leak out of it. If the attachment ruptures, there can be life-threatening hemorrhage. When a vascular grafting prosthesis becomes infected, it needs to be removed. It is especially dangerous to put another vascular grafting prosthesis in the same spot because of the risk of another infection, but there are often few other options. Vascular grafting prostheses comprising compounds of the invention can resist infections, thereby avoiding these devastating complications.

Vascular grafting prostheses of small caliber are particularly prone to clotting. A vascular grafting prosthesis comprising a compound of the invention may not only prevent biofilm formation, but also inhibit clotting as described above, allowing a smaller diameter vascular grafting prosthesis to be more reliable. A common site for clotting is the junction point between the vascular grafting prosthesis and the normal vessel, called the anastomosis. Even if an artificial vascular grafting prosthesis is not used, anywhere that two vessels are joined or anywhere there is a suture line that penetrates a natural blood vessel, there is a potential for clotting to take place. A clot in a vessel can occlude the vessel entirely or only partially; in the latter case, blood clots can be swept downstream, damaging local tissues. Using suture comprised of the compounds of the invention may inhibit clotting at these various suture lines. The smaller the vessel, the more likely that a clot forming within it will lead to a total occlusion. This can have disastrous results: if the main vessel feeding a tissue or an organ becomes totally occluded, that structure loses its blood supply and can die. Microsurgery provides dramatic examples of the damage that can occur with anastomotic clotting. In microsurgery, typically only a single tiny vessel is feeding an entire tissue structure like a finger or a muscle. If the vessel clots off, the tissue structure can quickly die. Microsurgery typically involves vessels only one to four millimeters in diameter. It is understood that the sutures penetrating the vessel at the anastomosis are likely sites for clots to form. Microsurgical sutures comprising a compound of the invention would result in localized administration of an anticoagulant at the site most likely to be damaged by clotting.

Suture material used to anchor vascular grafting prostheses to normal blood vessels or to sew vessels or other structures together can also harbor infections. Sutures used for these purposes are commonly made of prolene, nylon or other monofilamentous nonabsorbable materials. An infection that begins at a suture line can extend to involve the vascular grafting prosthesis. Suture materials comprising a compound of the invention would have increased resistance to infection.

A suture comprising a compound of the invention would be useful in other areas besides the vasculature. Wound infections at surgical incisions may arise from microorganisms that lodge in suture materials placed at various levels to close the incision. General surgery uses both nonabsorbable and absorbable sutures. Materials for nonabsorbable sutures include prolene and nylon. Absorbable sutures include materials like treated catgut and polyglycolic acid. Absorbable sutures retain tensile strength for periods of time from days to months and are gradually resorbed by the body. Fabricating an absorbable or a nonabsorbable suture comprising a compound of the invention and which retains the handling and tensile characteristics of the material is within the skill of artisans in the field.

Medical prostheses comprising compounds of the invention would be expected to have reduced contamination and subsequent local infection, thereby obviating or reducing the need to remove the implant with the attendant destruction of local tissues. Destruction of local tissues, especially bones and ligaments, can make the tissue bed less hospitable for supporting a replacement prosthesis. Furthermore, the presence of contaminating microorganisms in surrounding tissues makes recontamination of the replacement prosthesis easily possible. The effects of repeated contamination and infection of structural prosthetics is significant: major reconstructive surgery may be required to rehabilitate the area in the absence of the prosthesis, potentially including free bone transfers or joint fusions. Furthermore, there is no guarantee that these secondary reconstructive efforts will not meet with infectious complications as well. Major disability, with possible extremity amputation, is the outcome from contamination and infection of a structural prosthesis.

Tissue expanders are sacs made of silicone elastomers adapted for gradual filling with a saline solution, whereby the filling process stretches the overlying tissues to generate an increased area of tissue that can be used for other reconstructive applications. Tissue expanders can be used, for example, to expand chest wall skin and muscle after mastectomy as a step towards breast reconstruction. Tissue expanders can also be used in reconstructing areas of significant skin loss in burn victims. A tissue expander is usually intended for temporary use: once the overlying tissues are adequately expanded, they are stretched to cover their intended defect. If a tissue expander is removed before the expanded tissues are transposed, though, all the expansion gained over time is lost and the tissues return nearly to their pre-expansion state. The most common reason for premature tissue expander removal is infection. These devices are subjected to repeated inflations of saline solution, introduced percutaneously into remote filling devices that communicate with the expander itself. Bacterial contamination of the device is thought to occur usually from the percutaneous inflation process. Once contamination is established and a biofilm forms, local infection is likely. Expander removal, with the annulment of the reconstructive effort, is needed to control the infection. A delay of a number of months is usually recommended before a new tissue expander can be inserted in the affected area. The silicone elastomer used for these devices is especially suitable for integrating with sulfate ester AF agents. Use of these agents in the manufacture of these articles may reduce the incidence of bacterial contamination, biofilm development and subsequent local infection.

Insertable devices include those objects made from synthetic materials applied to the body or partially inserted into the body through a natural or an artificial site of entry. Examples of articles applied to the body include contact lenses and stoma appliances. An artificial larynx is understood to be an insertable device in that it exists in the airway, partially exposed to the environment and partially affixed to the surrounding tissues. An endotracheal or tracheal tube, a gastrostomy tube or a catheter are examples of insertable devices partially existing within the body and partially exposed to the external environment. The endotracheal tube is passed through an existing natural orifice. The tracheal tube is passed through an artificially created orifice. Under any of these circumstances, the formation of biofilm on the device permits the ingress of microorganisms along the device from a more external anatomic area to a more internal anatomic area. The ascent of microorganisms to the more internal anatomic area commonly causes local and systemic infections.

As an example, biofilm formation on soft contact lenses is understood to be a risk factor for contact-lens associated corneal infection. The eye itself is vulnerable to infections due to biofilm production. Incorporating an antifouling agent in the contact lens itself and in the contact lens case can reduce the formation of biofilms, thereby reducing risk of infection. Sulfate ester AF agents can also be incorporated in ophthalmic preparations that are periodically instilled in the eye.

As another example, biofilms are understood to be responsible for infections originating in tympanostomy tubes and in artificial larynxes. Biofilms further reside in tracheostomy tubes and in endotracheal tubes, permitting the incursion of pathogenic bacteria into the relatively sterile distal airways of the lung. These devices are adaptable to the incorporation or the topical application of sulfate ester AF agents to reduce biofilm formation and subsequent infectious complications.

As another example, a wide range of vascular catheters are fabricated for vascular access. Temporary intravenous catheters are placed distally, while central venous catheters are placed in the more proximal large veins. Catheter systems can include those installed percutaneously whose hubs are external to the body, and those whose access ports are buried beneath the skin. Examples of long-term central venous catheters include Hickman catheters and Port-a-caths. Catheters permit the infusion of fluids, nutrients and medications; they further can permit the withdrawal of blood for diagnostic studies or the transfusion of blood or blood products. They are prone to biofilm formation, increasingly so as they reside longer within a particular vein. Biofilm formation in a vascular access device can lead to the development of a blood-borne infection as planktonic organisms disseminate from the biofilm into the surrounding bloodstream. Further, biofilm formation can contribute to the occlusion of the device itself, rendering it non-functional. If the catheter is infected, or if the obstruction within it cannot be cleared, the catheter must be removed. Commonly, patients with these devices are afflicted with serious medical conditions. These patients are thus poorly able to tolerate the removal and replacement of the device. Furthermore, there are only a limited number of vascular access sites. A patient with repeated catheter placements can run out of locations where a new catheter can be easily and safely placed. Incorporation of sulfate ester AF agents within catheter materials or application of these agents to catheter materials can reduce fouling and biofilm formation, thereby contributing to prolonged patency of the devices and minimizing the risk of infectious complications.

As another example, a biliary drainage tube is used to drain bile from the biliary tree to the body's exterior if the normal biliary system is blocked or is recovering from a surgical manipulation. Drainage tubes can be made of plastics or other polymers. A biliary stent, commonly fabricated of a plastic material, can be inserted within a channel of the biliary tree to keep the duct open so that bile can pass through it. Biliary sludge which forms as a result of bacterial adherence and biofilm formation in the biliary system is a recognized cause of blockage of biliary stents. Pancreatic stents, placed to hold the pancreatic ducts open or to drain a pseudocyst of the pancreas, can also become blocked with sludge. Biofilms are furthermore implicated in the ascent of infections into the biliary tree along a biliary drainage tube. Ascending infections in the biliary tree can result in the dangerous infectious condition called cholangitis. Incorporation of compounds of the invention in the materials used to form biliary drainage tubes and biliary stents can reduce the formation of biofilms, thereby decreasing risk of occlusions and infections.

As another example, a peritoneal dialysis catheter is used to remove bodily wastes in patients with renal failure by using fluids instilled into and then removed from the peritoneal cavity. This form of dialysis is an alternative to hemodialysis for certain renal failure patients. Biofilm formation on the surfaces of the peritoneal dialysis catheter can contribute to blockage and infection. An infection entering the peritoneal cavity is termed a peritonitis, an especially dangerous type of infection. Peritoneal dialysis catheters, generally made of polymeric materials like polyethylene, can be coated with or impregnated with sulfate ester AF agents to reduce the formation of biofilms.

As yet another example, a wide range of urological catheters exist to provide drainage of the urinary system. These catheters can either enter the natural orifice of the urethra to drain the bladder, or they can be adapted for penetration of the urinary system through an iatrogenically created insertion site. Nephrostomy tubes and suprapubic tubes represent examples of the latter. Catheters can be positioned in the ureters on a semipermanent basis to hold the ureter open; such a catheter is called a ureteral stent. Urological catheters can be made from a variety of polymeric products. Latex and rubber tubes have been used, as have silicones. All catheters are susceptible to biofilm formation. This leads to the problem of ascending urinary tract infections, where the biofilm can spread proximally, carrying pathogenic organisms, or where the sessile organisms resident in the biofilm can propagate planktonic organisms that are capable of tissue and bloodstream invasion. Organisms in the urinary tract are commonly gram-negative bacteria capable of producing life-threatening bloodstream infections if they spread systemically. Infections wherein these organisms are restricted to the urinary tract can nonetheless be dangerous, accompanied by pain and high fever. Urinary tract infections can lead to kidney infections, called pyelonephritis, that can jeopardize the function of the kidney. Incorporating sulfate ester AF agents can inhibit biofilm formation and may reduce the likelihood of these infectious complications.

A further complication encountered in urological catheters is encrustation, a process by which inorganic compounds comprising calcium, magnesium and phosphorous are deposited within the catheter lumen, thereby blocking it. These inorganic compounds are understood to arise from the actions of certain bacteria resident in biofilms on catheter surfaces. Reducing biofilm formation by the action of sulfate ester AF agents may contribute to reducing encrustation and subsequent blockage of urological catheters.

Other catheter-like devices exist that can be treated with AF agents. For example, surgical drains, chest tubes, hemovacs and the like can be advantageously treated with materials to impair biofilm formation. Other examples of such devices will be familiar to ordinary practitioners in these arts.

Materials applied to the body can advantageously employ the AF compounds disclosed herein. Dressing materials can themselves incorporate the AF compounds, as in a film or sheet to be applied directly to a skin surface. Additionally, AF compounds of the instant invention can be incorporated in the glue or adhesive used to stick the dressing materials or appliance to the skin. Stoma adhesive or medical-grade glue may, for example, be formulated to include an AF agent appropriate to the particular medical setting. Stoma adhesive is used to adhere stoma bags and similar appliances to the skin without traumatizing the skin excessively. The presence of infectious organisms in these appliances and on the surrounding skin makes these devices particularly appropriate for coating with AF agents, or for incorporating AF agents therein. Other affixation devices can be similarly treated. Bandages, adhesive tapes and clear plastic adherent sheets are further examples where the incorporation of an AF agent in the glue or other adhesive used to affix the object, or incorporation of an AF agent as a component of the object itself, may be beneficial in reducing skin irritation and infection.

These above examples are offered to illustrate the multiplicity of applications of compounds of the invention in medical devices. Other examples will be readily envisioned by skilled artisans in these fields. The scope of the present invention is intended to encompass all those surfaces where the presence of fouling has adverse health-related consequences. The examples given above represent embodiments where the technologies of the present invention are understood to be applicable. Other embodiments will be apparent to practitioners of these and related arts. Embodiments of the present invention can be compatible for combination with currently employed antiseptic regimens to enhance their antimicrobial efficacy or cost-effective use. Selection of an appropriate vehicle for bearing a compound of the invention will be determined by the characteristics of the particular medical use. Other examples of applications in medical environments to promote antisepsis will be readily envisioned by those of ordinary skill in the relevant arts.

Antifouling coating compositions of the present invention can also contain a paint base such as rosin, silicone, vinyl, acrylic, and alkyd resin bases. They can also contain a pigment such as titanium dioxide, a thickener such as bentonite, fillers such as aluminum silicate and calcium silicate, and driers such as cobalt naphthenate and manganese naphthenate. They may also contain solvents or thinners such as mineral spirits, naphtha, benzene, toluene, methylethyl ketone, and the like.

Biological contamination on food processing surfaces is a potential source of bacterial contamination of foods and can result in decreased shelf life or transmission of disease. The possible presence of biological contamination on medically related devices, such as surgical and medical instruments, implants and prosthetics is also of serious concern. It would also be desirable to treat surfaces of a variety of other materials, e.g., upholstery fabrics, plastic food packaging films, and so forth, to make them resistant to the deposit and adhesion of bacteria and other biological materials.

Due to their ability to interfere with the attachment of organisms to surfaces, the compounds of the present invention have broad applicability in inhibiting a variety of organisms that contribute to the formation of biofilms or are otherwise involved with biofouling. Additionally, the compounds of the instant invention have utility as environmentally benign crop protection agents because they are capable of preventing attack of various fingi species upon seeds, seedlings, and mature crop plants, and bacteria.

Further, adhesion of pathologic biologics to the surface of host cells is often a required step in the pathogenesis of disease. Therefore, substances, such as the compounds of the instant invention, that interfere with the ability of pathologic microorganisms to adhere to the surface of host cells may have use in preventing initiation of cellular infection.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

Combinatorial Libraries

The subject methods readily lend themselves to the creation of combinatorial libraries of compounds for the screening of pharmaceutical, agrochemical or other biological or medical activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.*

14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381-5383), and an example of such a library appeared the following year (Needles et al. (1993) PNAS 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529-2531), orthogonality in synthesis is achieved by employing acid-labile protection for the coding strand and base-labile protection for the compound strand.

In an alternative approach (Nikolaiev et al. (1993) Pept Res 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) PNAS 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

General Procedure for Screening Compounds for Activity

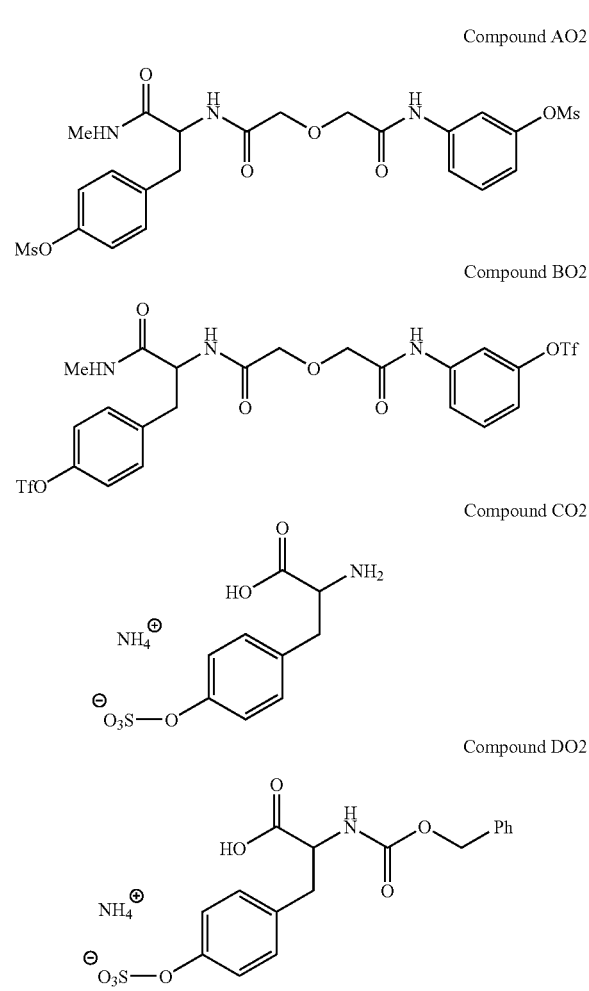

The results of screening the four compounds shown above are representative. Compounds were packaged in 2-5 mg quantities in wells A02-D02 of a 96-deep well polypropylene microplate, tightly sealed with a plastic dimpled lid. The four compounds were handled under slightly different conditions as they fell into two solubility classes. Compounds A02 and B02, insoluble in water, were dissolved in DMSO and tested at a final concentration of 0.5% with 5% DMSO, a concentration of DMSO that has no effect on any of the organisms used in the assays. Compounds C02 and D02, soluble in water, were dissolved in E-pure water, and tested at 0.5% after having been adjusted to the proper buffer condition for the assay. The compounds were tested in three species, *Staphylococcus epidermidis*, important in human pathology, *Colletotrichum* acutatum, a plant pathogenic fungus, and *Pseudoalteramonas atlantica*, a marine biofouling bacterium. The two bacteria were tested using a 96-well multiwell plate protocol, using the fluorescent dye, Syto 13, to quantitate the assay. The fungus was tested in a 35 mm petri dish protocol using spore counts to quantitate the test. Methods for assays testing for activity against *Staphylococcus*, *Pseudoalteramonas*, and *Colletotrichum* species are described in Examples 3, 4, and 5, respectively. Results of the assays are reported in Example 2.

Example 2

Inhibition of Adhesion of Cells or Spores to Polystyrene Surfaces

The results tabulated herein were generated using the protocol described in Example 1.

| Compound | Staphylococcus epidermidis | Pseudoalteramonas atlantica | Colletotrichum acutatum |
|---|---|---|---|
| Compound A02 | 22% | | −12% |
| Compound B02 | | | −16% |
| Compound C02 | 6% | | −36% |
| Compound D02 | 74% | 32% | −19% |

Example 3

96-Well Plate Assay for Activity Against *Staphyloccocus epidermidis*

Reagents Used:

| 10XPBS | 80 g | NaCl | 1 L |
|---|---|---|---|
| | 2 g | $KH_2PO_4$ | |
| | 11.35 g/21.4 g | $Na_2HPO_4$/$Na_2HPO_4$ $7H_2O$ | |
| | 2 g | KCl | |
| | pH 7.2 | | |
| SYTO 13 | 5 mM in DMSO | | |
| LB growth media | | | |

1. *S. epidermidis* (ATCC #12228) is grown on nutrient agar plates from −70° C. stock, a single colony should be picked and subcultured in LB media for overnight growth at 37° C. shaking 200 rpm.

2. Next day use $\frac{1}{100}^{th}$ volume of overnight culture to start new culture, this culture will need to grow for 4-5 hr which will be early log phase of growth.

3. Pour culture into 50 mL conical tubes and centrifuge at 3000 rpm for 10 min at R.T., pour off supernatant and gently re-suspend pellet in 0.5 volume of original culture with 1×PBS buffer.

4. Use this re-suspended culture to determine OD using the Shimadzu spectrophotometer and dilute cells to 1 OD at 600 nm.

5. Experimental controls and samples need to be added to wells prior to adding cells, positive control at 2%, 1%, and 0.1% added to three wells each.

6. Dynex 96 well black solid bottom plates are used for the fluorescence assay. Prep standard curve wells by adding 50 uL of 1×PBS in each well, 15 wells are needed for a 1:1 dilution series starting at 0.5-0.03125 OD of cells in triplicate. Make dilutions and add the Syto 13 probe (1 uM final) fresh just before adding to the wells. The 9 wells below standards need to be saved for background controls, these also will need the probe as well.

7. Working O.D. will be 0.0625 OD and Syto 13 probe is 1 uM final, well volume is 100 uL. Once experimental samples have been incubated in the wells for a minimum of 10 min then add cells to each well according to final volume and concentrations.

8. Incubate cells on plate for 25 min then wash on Tecan Plate washer 5 cycles of 300 uL rinse with 1×PBS solution. At last cycle dispense 100 uL of 1×PBS solution and read fluorescence.

9. Excitation is 488 nm and Emission at 509 nm, use the Tecan Microfluor Fluorescein setting.

Example 4

96-Well-Plate Assay for Activity Against *Pseudoalteromonas atlantica*

1. Media and Reagent Preparation:
   Marine broth (Defico 2216): Medium prepared according to the manufacture's instructions and autoclaved for 20 min. There was precipitation after cooling. Let sit for 1-2 days and transfer the clear part to a sterile bottle and store at RT.
   80% seawater: It can be either filtered natural seawater (FSW) or artificial seawater (ASW, sigma S-9883). Autoclave to sterilize and store at RT.
   PBS: see Example 3.
   1 uM Syto-13: add 1 ul of 5 mM stock (in DMSO) from Molecular Probe (Cat#7575) to every 5 ml PBS.

2. Preparation for Cell Material:
   Cultured in sterile marine broth in late afternoon (ca. 5-6 pm) one day before assaying. Grown at 26-29° C. in a shaking incubator (200 rpm).
   Harvested the cells next morning when the OD600 of the culture reaches 0.7-1.0, using centrifugation (3000 rpm, 10 min, RT). Cell pellets normally only loosely piled on the bottom the felcon tubes. So be careful when taking out the supernatant. Inverting the tubes to pour out the supernatant is not recommended.
   Resuspend the cells with 80% seawater to OD between 0.3 to 1.0, then use the cell preparation within an hour.

3. Assaying Procedure:
   Dynex total-black plate and Nunc total-black plate (with or without coating) work well. But Nunc total-black plate coated is the best.
   Made solutions containing ZA double concentrated as intended to use, using 80% seawater.
   Added 50 ul of the solutions to each well on the plate. Added just 50 ul of 80% seawater to the wells as control.
   Then added 50 ul of the cell preparation described above into those wells. Shook the plate briefly to make sure that cells are mixed with ZA solution.
   Incubated the plate at RT for 40 min (no shaking is needed).
   After incubation, washed the plate with the plate-washer using 80% seawater (program 3, which is a 5 cycle wash), and then add 100 ul of 1 uM Syto-13 in PBS into each well.
   Incubated the plate with the dye solution for 15 min in darkness or at least under dim light.

Read the plate with Tecan using the program "Syto-13" (Excitation is 488 nm and Emission at 509 nm). Set the gain at either 100 or optimal.

Example 5

Petri Dish Assay for Activity Against *Colletotrichum acutatum*

Reagents:

Tap water

50/50 Oatmeal/PDA agar plates

1. *C. acutatum* was grown on 50/50 oatmeal. PDA agar plates for 6-8 days. Seven days are optimal. Regular inoculations of plates can be made from plate to plate, but new stocks should be brought up from the frozen stock every two months.

10. Flooded plate with 10-15 ml tap water, pipetting wash gently over the culture to tease the spores loose.

11. Transferred wash into 15 or 50 ml conical tubes and centrifuge at 3000 rpm for 5 min at R.T., pour off supernatant and vortex pellet in 10 ml of tap water to resuspend pellet.

12. Counted spores at a 1:100 dilution, using a haemocytometer. Counts generally are $6-8 \times 10^7$ spores/ml. Dilute spores to $2 \times 10^5$ spores/ml; about 35 µl/10 ml tap water. Refrigerate spore suspensions.

13. For experiment, data points were staggered at 15 min intervals. Set up three eppendorf tubes. Add 100 µl of test compound made up in e-pure water to the tube. Add 100 µl of spore suspension to the tubes.

14. Allowed to equilibrate for 15 min. Transfer 100 µl from each tube to a 35 mm Falcon petri dish which has been labeled and marked with a graphic on the bottom to orient the plate. Place the drop in the center of the graphic.

15. At 55 minutes took 5 images of the spores on the surface of the petri dish.

16. At 1 hr after the spores were originally put into the eppendorf tubes, washed spores from petri dish by adding three ml of e-pure water to each dish and vortex dishes on the microplate shaker at a setting of 900 rpm for 30 seconds. Take an additional 5 images per dish following the same pattern as in step 6. There should be ~200-500 spores/field.

Note. If individual data points are staggered by 15 minutes, there is adequate time to photograph the plates, transfer a set from eppendorf tubes to petri dish and set up a new set of tubes between time points. If the experiment is large, a new dilution of spores should be made after each 2-2.5 hrs, as the spores adhere to the 15 ml tube, reducing the spore count in a time dependent manner.

17. Counted the spores in the images using the Image Pro software, enter the counts into the Excel template set up for this assay, which also calculates the % inhibition for each experimental point.

Example 6

Combinatorial Library

A combinatorial library was synthesized containing compounds having structures according to Template 6, shown below.

Template 6

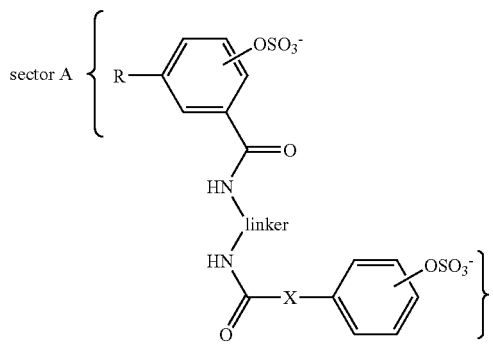

R was either H, Cl, or OMe. The linker comprised a saturated or unsaturated hydrocarbon tether consisting of between 2 and about 15 carbon atoms, which tether may comprise an aromatic nucleus. For example, 1,4-piperazine and propane-1,3-diamine were used as linkers. X was a bond or (E)—CH═CH—.

The aromatic nucleus of Sector A was derived from any of the following four methyl benzoates:

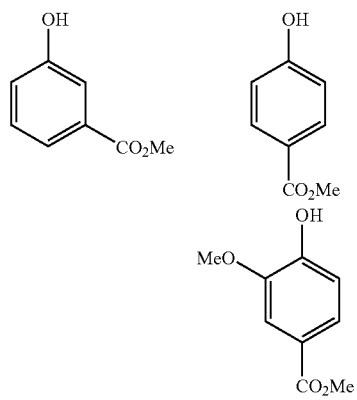

X and the aromatic nucleus of Sector B was derived from any of the following β-phenyl acrylic acids:

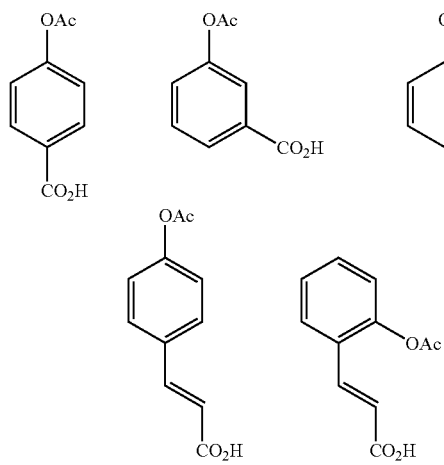

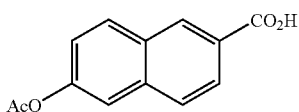

Members of this combinatorial library were synthesized as shown below.

Example 6A

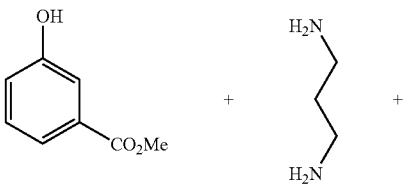

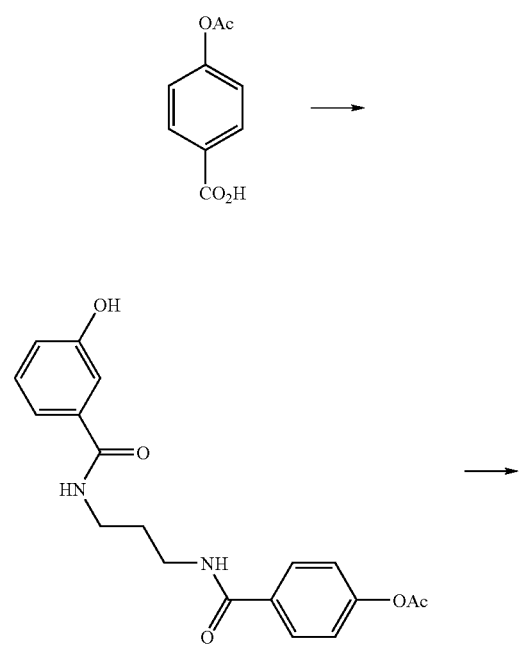

1. deprotection
2. sulfation

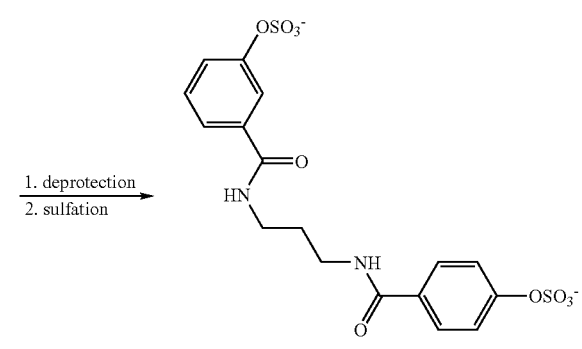

43
Example 6B
44
Example 6C
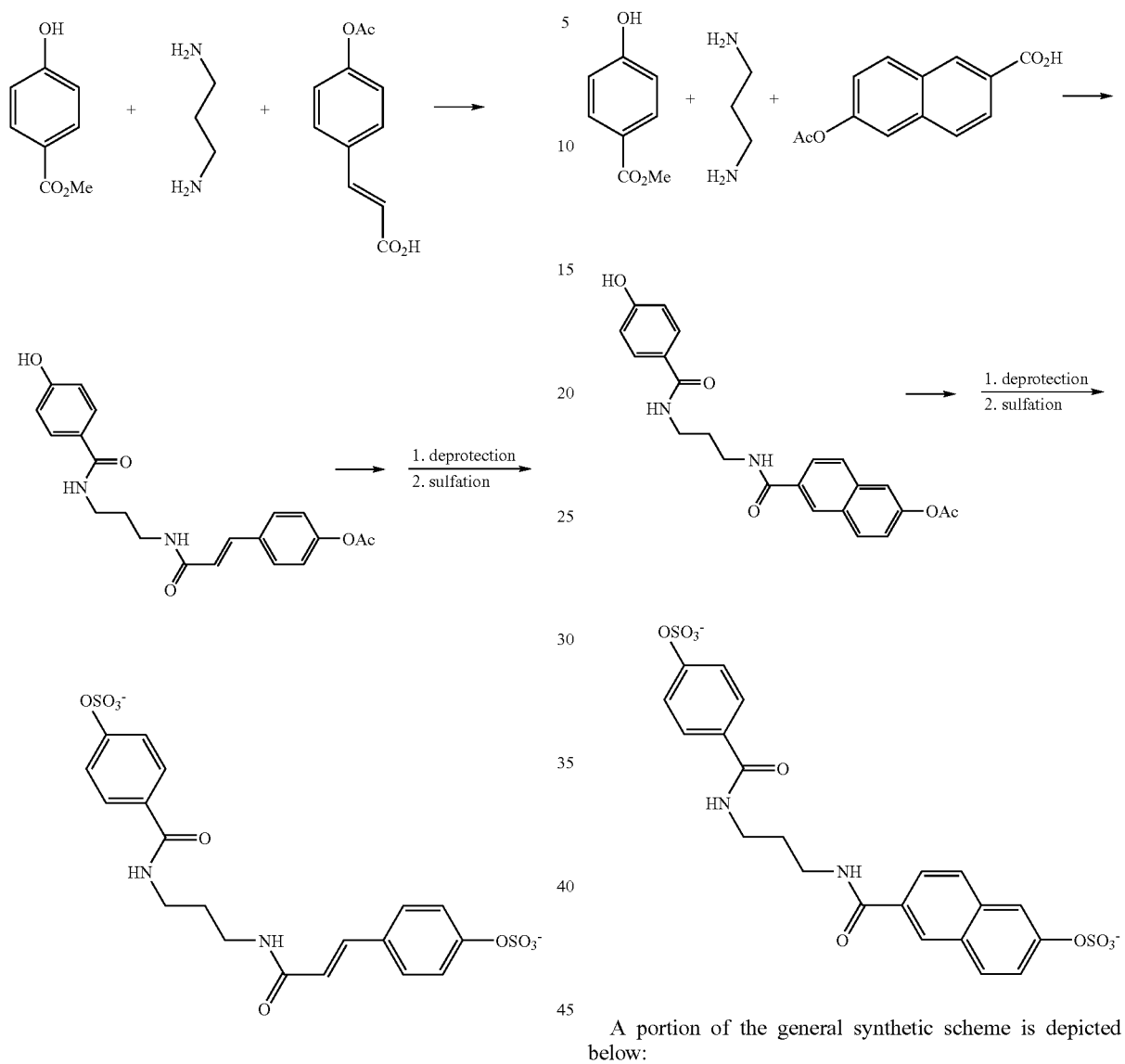
A portion of the general synthetic scheme is depicted below:
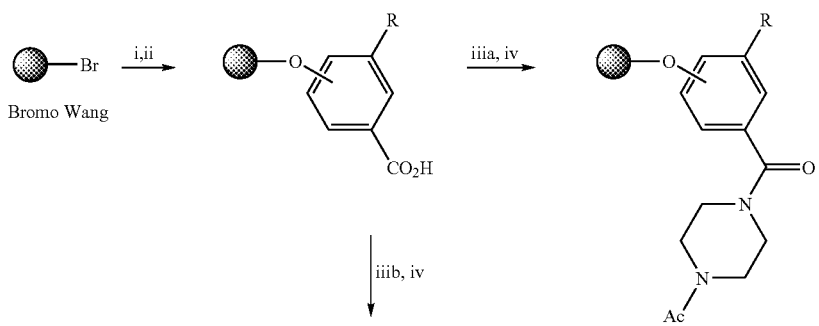

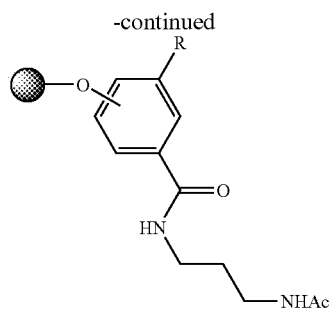

Key: (i) Methyl benzoate, KOtBu, DMA; (ii) LiOH, THF MeOH, H₂O (6:2:1), 65 deg C.
(iii) linker diamine, DIC, HOBt, DCM:DMF (2:1),
  (iiia) piperazine a diamine,
  (iiib) 1,3-diaminopropane as diamine;
(iv) Ac₂O, DCM:DMF: (2:1)

Example 7

Combinatorial Library

A combinatorial library was synthesized containing compounds having structures according to Template 7, shown below:

Template 7

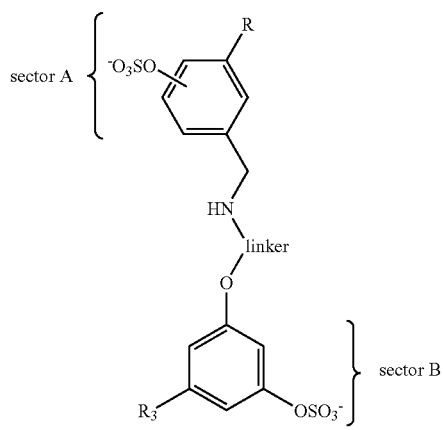

R was either H, Br, Me, OMe, or Cl. The aromatic nucleus of Sector A was derived from any of the following hydroxybenzaldehydes:

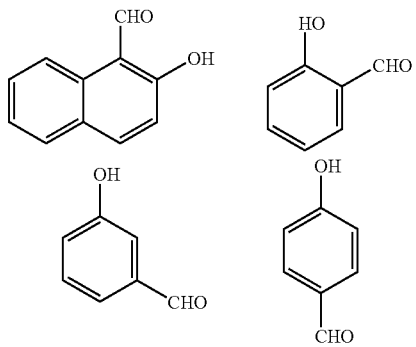

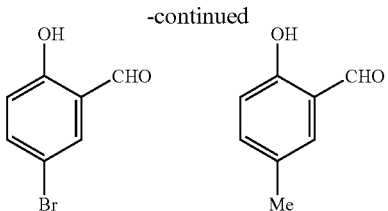

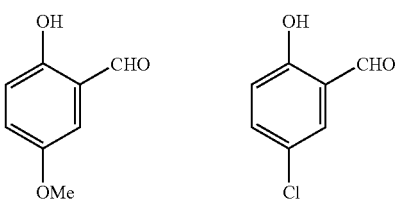

The linker was derived from any of the following amino alcohols:

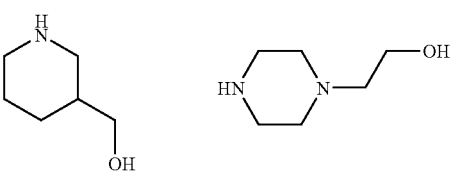

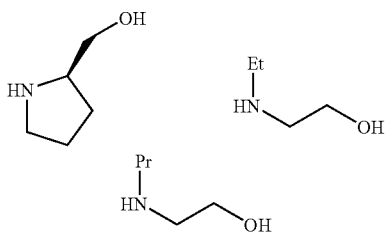

$R_3$ was either H, Me, or $CO_2Me$. The aromatic nucleus of Sector B was derived from any of the following compounds:

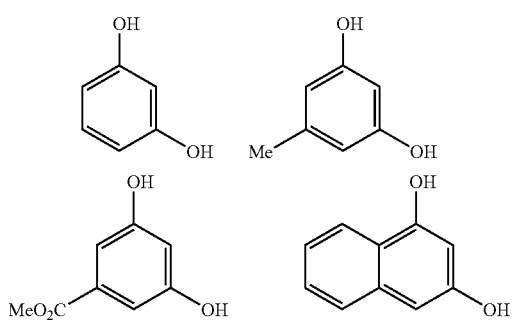
Members of this combinatorial library were synthesized as shown below:
Example 7A
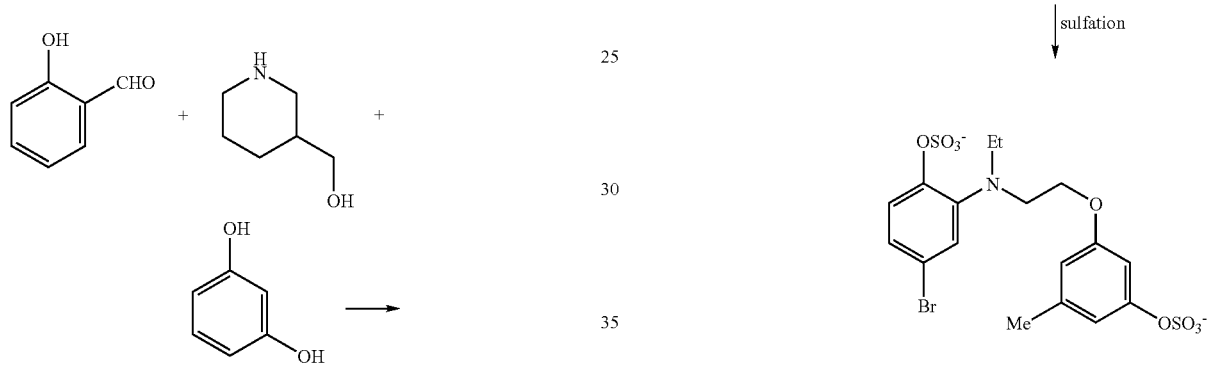
Example 7B
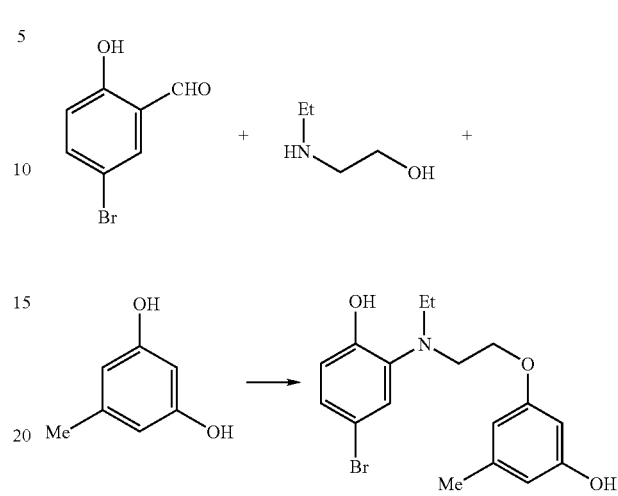
Example 7C
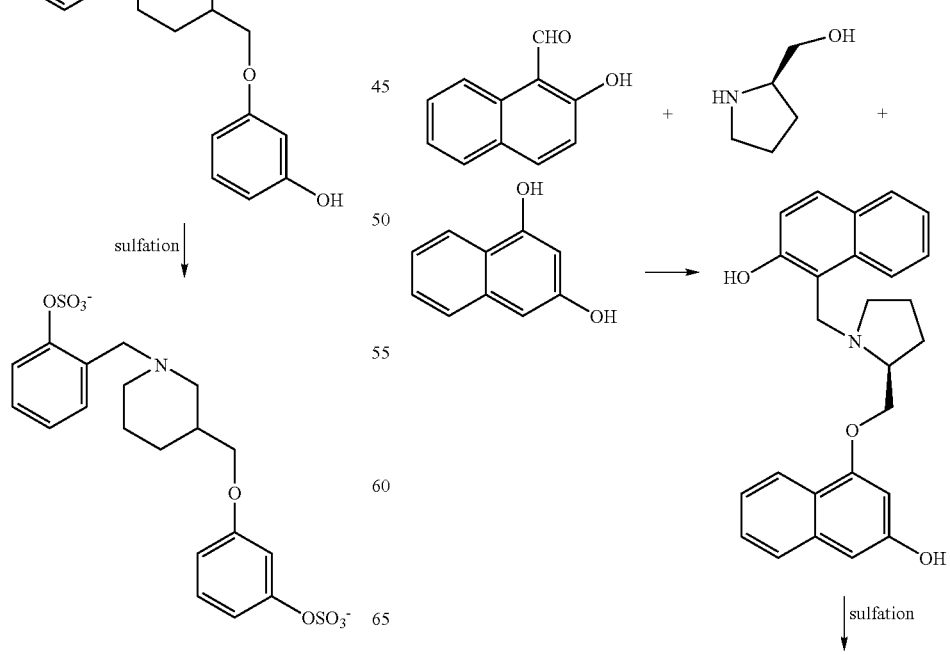

-continued

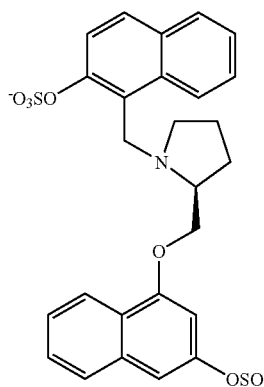

The general synthetic scheme for this library is depicted below:

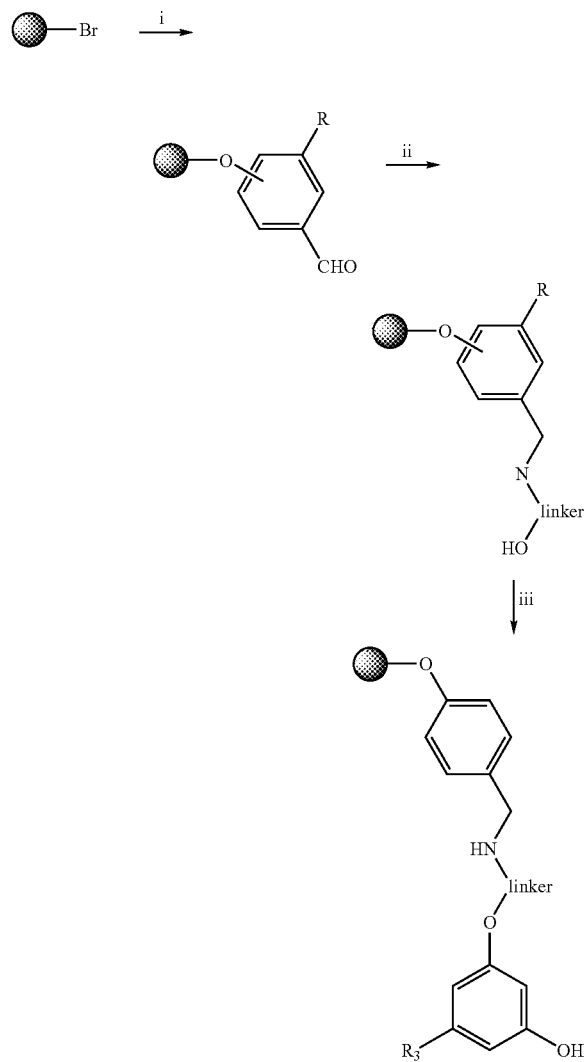

Key: (i) R hydroxybezaldehydes, KOtBu, DMF
(ii) amino alcohol, NaBH₃CN, 1%HOAc in DMF
(iii) R₃-substituted hydroxyphenols, DIAD, Ph₃P, solvent

Example 8

Combinatorial Library

A combinatorial library was synthesized containing compounds having structures according to Template 8, shown below:

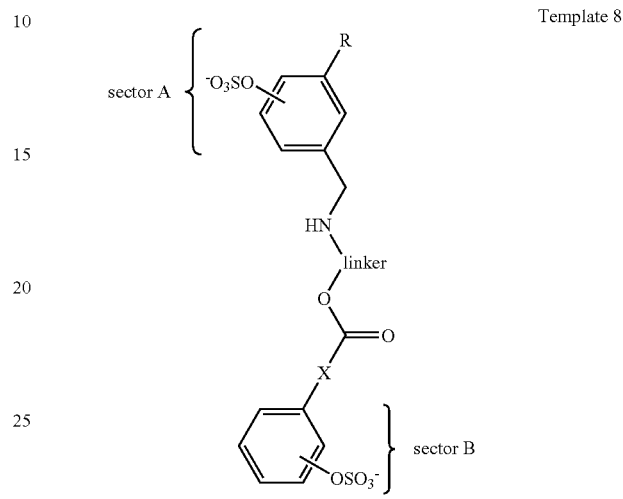

R was either H, Br, Me, OMe, or Cl. The aromatic nucleus of Sector A was derived from any of the following hydroxybenzaldehydes:

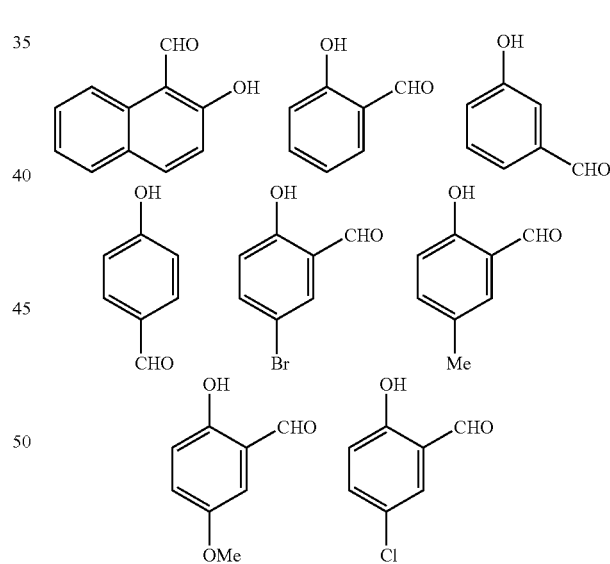

The linker was derived from any of the following amino alcohols:

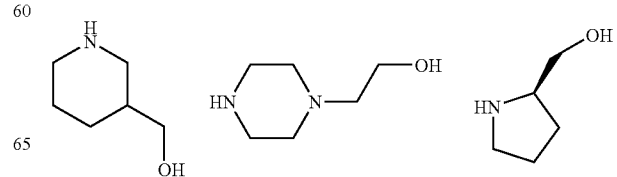

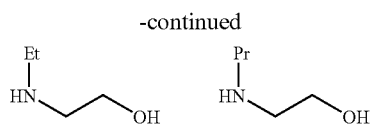
X and the aromatic nucleus of sector B was derived from any of the acetoxybenzoic acids, shown below:
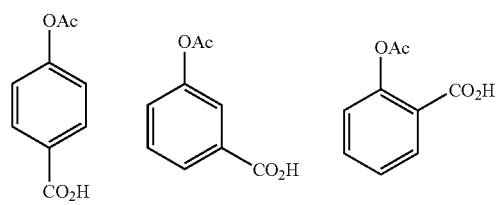
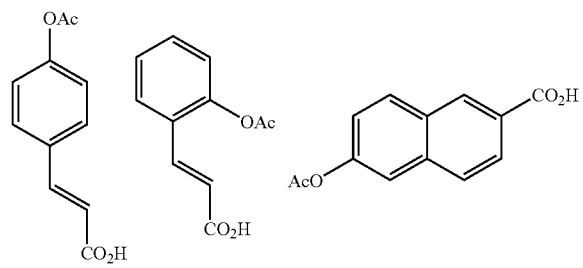
Members of this combinatorial library were synthesized as shown below:
Example 8A
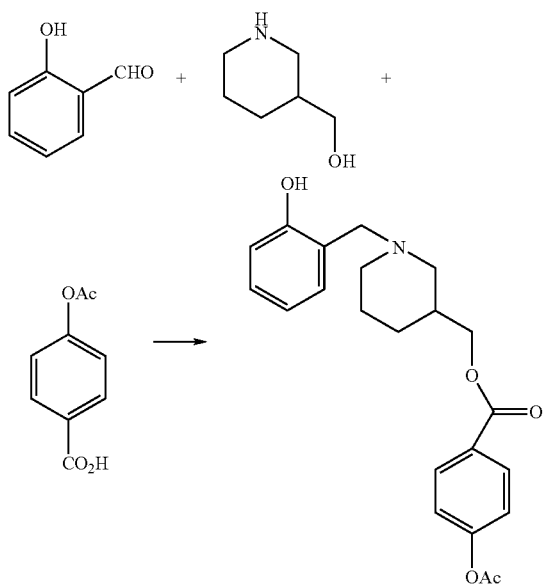
i) deprotection
ii) sulfation
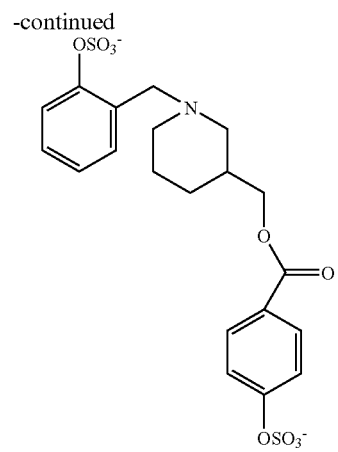
Example 8B
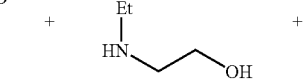
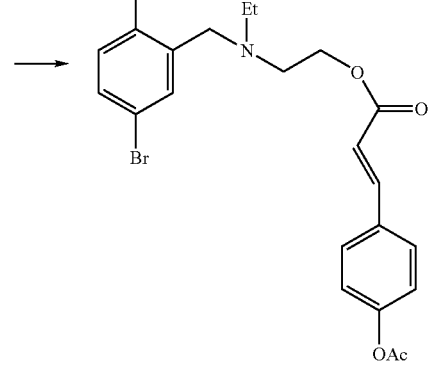
i) deprotection
ii) sulfation
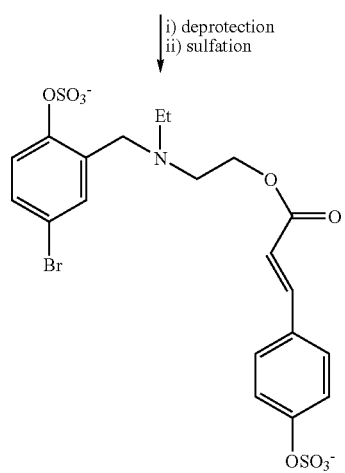

Example 8C

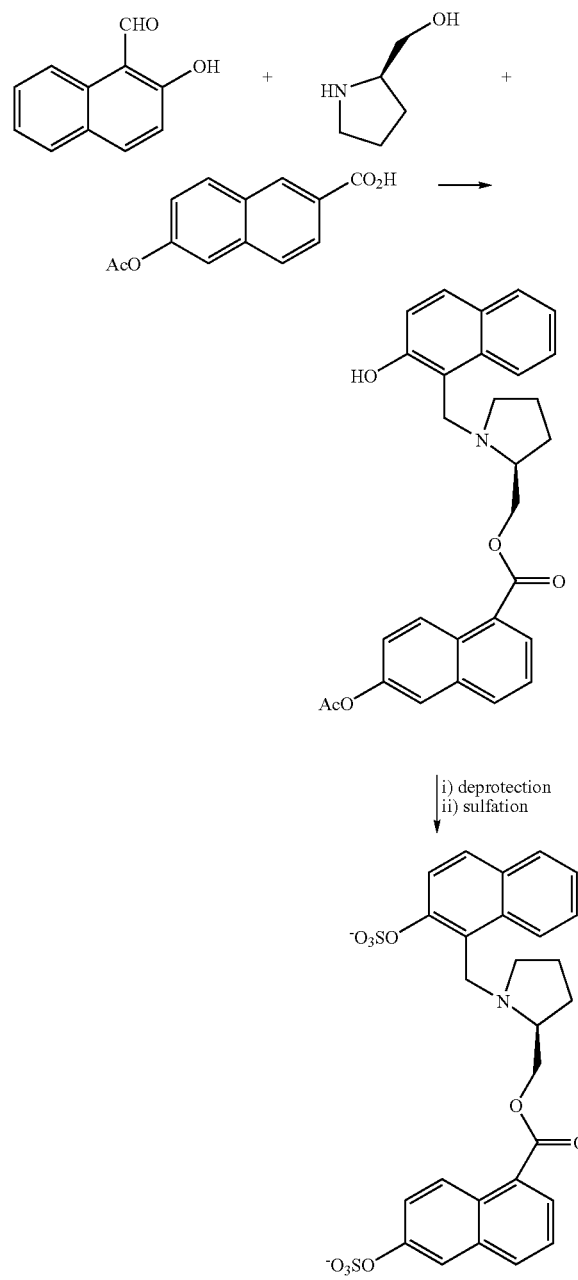

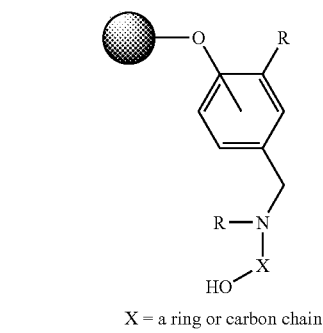

X = a ring or carbon chain

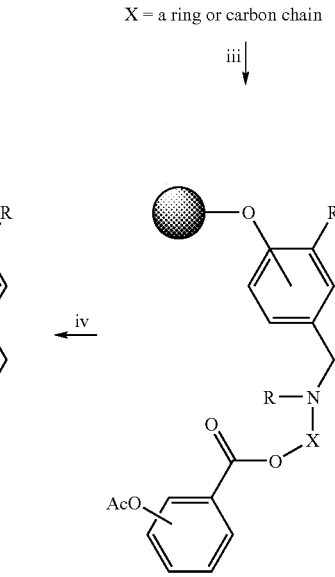

Key: (i) Hydroxybenzaldhyde, KOtBu, DMF (ii) amino alcohol, NaBH₃CN, 1% HOAc in DMF (iii)Acetoxybenzoic acids, DIC; (IV) selective hydrolysis

Example 9

Combinatorial Library

A combinatorial library was synthesized containing compounds having structures according to Template 9, shown below:

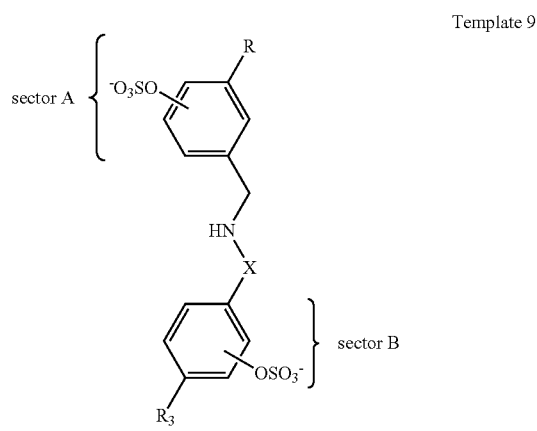

Template 9

The general synthetic scheme for this library is depicted below:

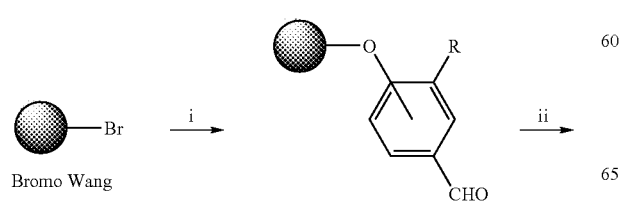

R was either H, Br, Me, OMe, or Cl. $R_3$ was either H or Me. The aromatic nucleus of sector A was derived from any of the following compounds:
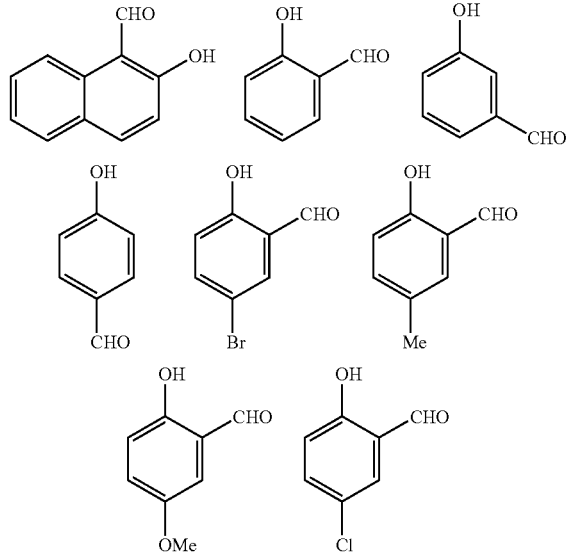
X and the aromatic nucleus of Sector B were derived from the following aryl amines:
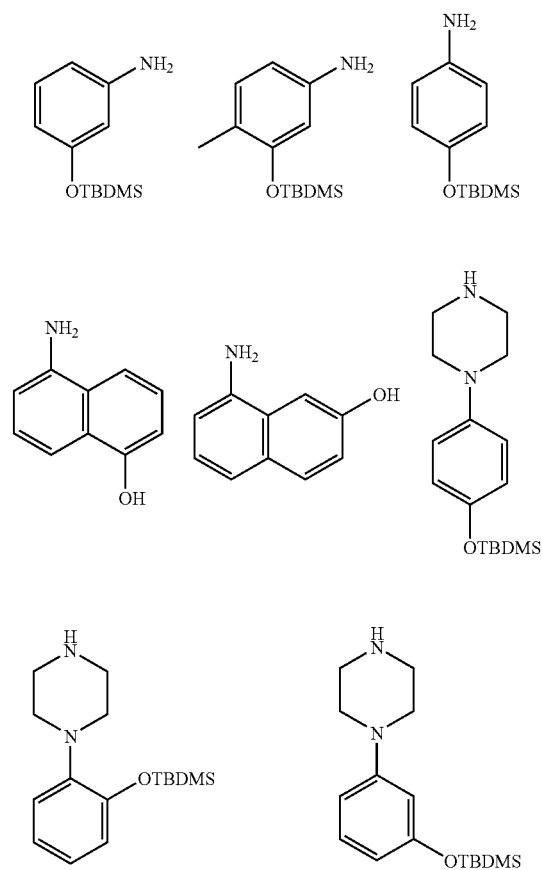
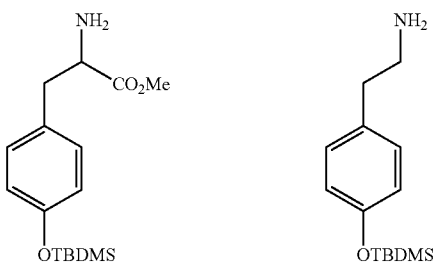
Members of this combinatorial library were synthesized as shown below:
Example 9A
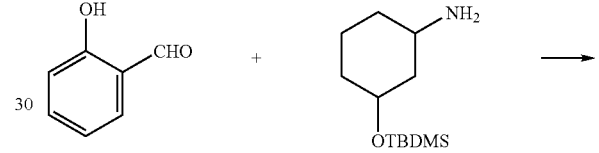
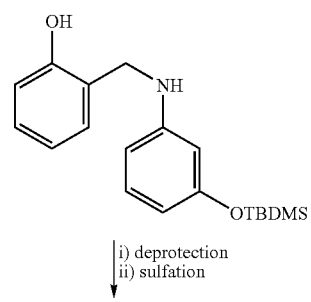
i) deprotection
ii) sulfation
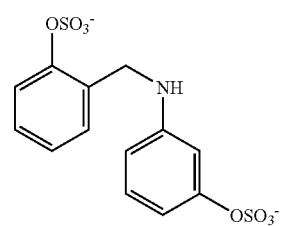

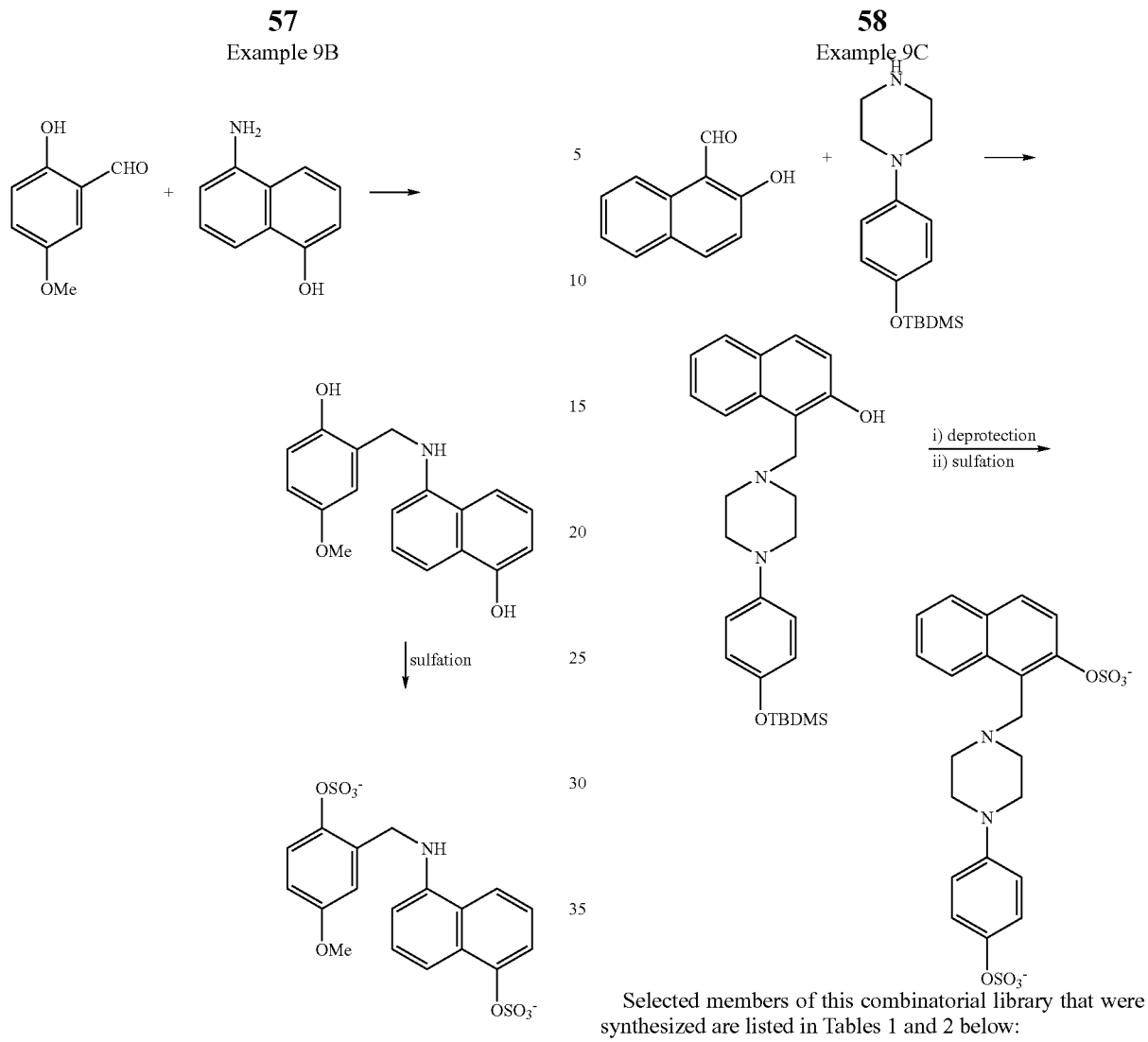

Selected members of this combinatorial library that were synthesized are listed in Tables 1 and 2 below:

TABLE 1

Mesylates according to Template 9:

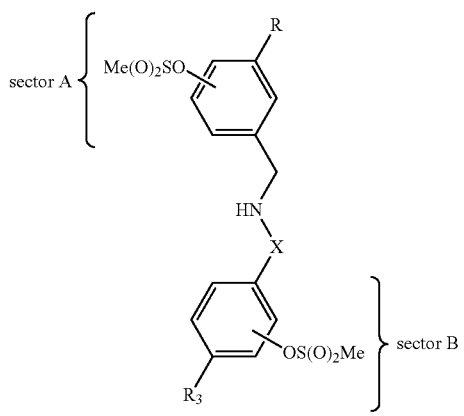

| Cmpd | Sector A derived from: | Sector B derived from: |
|---|---|---|
| 1 | SALICYLALDEHYDE | 1-(3-HYDROXYPHENYL)-PIPERAZINE |
| 2 | SALICYLALDEHYDE | N-(2-HYDROXYPHENYL)-PIPERAZINE |
| 3 | 3-HYDROXYBENZALDEHYDE | 1-(4-HYDROXYPHENYL)-PIPERAZINE |
| 4 | 3-HYDROXYBENZALDEHYDE | 1-(3-HYDROXYPHENYL)-PIPERAZINE |
| 5 | 3-HYDROXYBENZALDEHYDE | N-(2-HYDROXYPHENYL)-PIPERAZINE |

TABLE 1-continued

Mesylates according to Template 9:

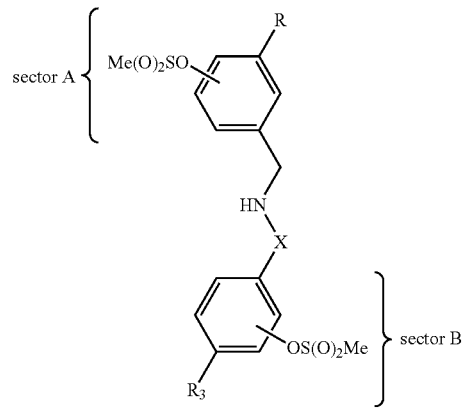

| Cmpd | Sector A derived from: | Sector B derived from: |
|---|---|---|
| 6 | 4-HYDROXYBENZALDEHYDE | 1-(4-HYDROXYPHENYL)-PIPERAZINE |
| 7 | 4-HYDROXYBENZALDEHYDE | 1-(3-HYDROXYPHENYL)-PIPERAZINE |
| 8 | 4-HYDROXYBENZALDEHYDE | N-(2-HYDROXYPHENYL)-PIPERAZINE |
| 9 | 2-HYDROXY-5-METHYLBENZALDEHYDE | 1-(4-HYDROXYPHENYL)-PIPERAZINE |
| 10 | 2-HYDROXY-5-METHYLBENZALDEHYDE | 1-(3-HYDROXYPHENYL)-PIPERAZINE |
| 11 | 2-HYDROXY-5-METHYLBENZALDEHYDE | N-(2-HYDROXYPHENYL)-PIPERAZINE |
| 12 | 2-HYDROXY-5-METHOXYBENZALDEHYDE | 1-(3-HYDROXYPHENYL)-PIPERAZINE |
| 13 | 2-HYDROXY-5-METHOXYBENZALDEHYDE | N-(2-HYDROXYPHENYL)-PIPERAZINE |
| 14 | 5-CHLOROSALICYLALDEHYDE | 1-(4-HYDROXYPHENYL)-PIPERAZINE |
| 15 | 5-CHLOROSALICYLALDEHYDE | 1-(3-HYDROXYPHENYL)-PIPERAZINE |
| 16 | 5-CHLOROSALICYLALDEHYDE | N-(2-HYDROXYPHENYL)-PIPERAZINE |
| 17 | 2-HYDROXY-1-NAPHTHALDEHYDE | 1-(4-HYDROXYPHENYL)-PIPERAZINE |
| 18 | 2-HYDROXY-1-NAPHTHALDEHYDE | 1-(3-HYDROXYPHENYL)-PIPERAZINE |
| 19 | 2-HYDROXY-1-NAPHTHALDEHYDE | N-(2-HYDROXYPHENYL)-PIPERAZINE |
| 20 | 5-BROMOSALICYLALDEHYDE | 1-(4-HYDROXYPHENYL)-PIPERAZINE |
| 21 | 5-BROMOSALICYLALDEHYDE | 1-(3-HYDROXYPHENYL)-PIPERAZINE |
| 22 | 5-BROMOSALICYLALDEHYDE | N-(2-HYDROXYPHENYL)-PIPERAZINE |

TABLE 2

Triflates accroding to Template 9:

| Compound | Sector A derived from: | Sector B deriuved from: |
|---|---|---|
| 1 | 3-HYDROXYBENZALDEHYDE | 1-(3-HYDROXYPHENYL)-PIPERAZINE |
| 2 | 5-BROMOSALICYLALDEHYDE | 1-(3-HYDROXYPHENYL)-PIPERAZINE |

Example 10

Combinatorial Library

A combinatorial library was synthesized containing compounds having structures according to Template 3, shown below.

Template 3

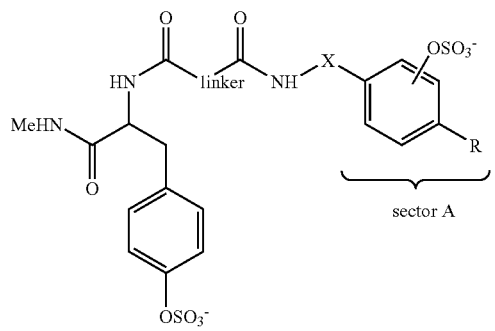

The linker was derived from any of the 24 diacids and cyclic anhydrides shown below.

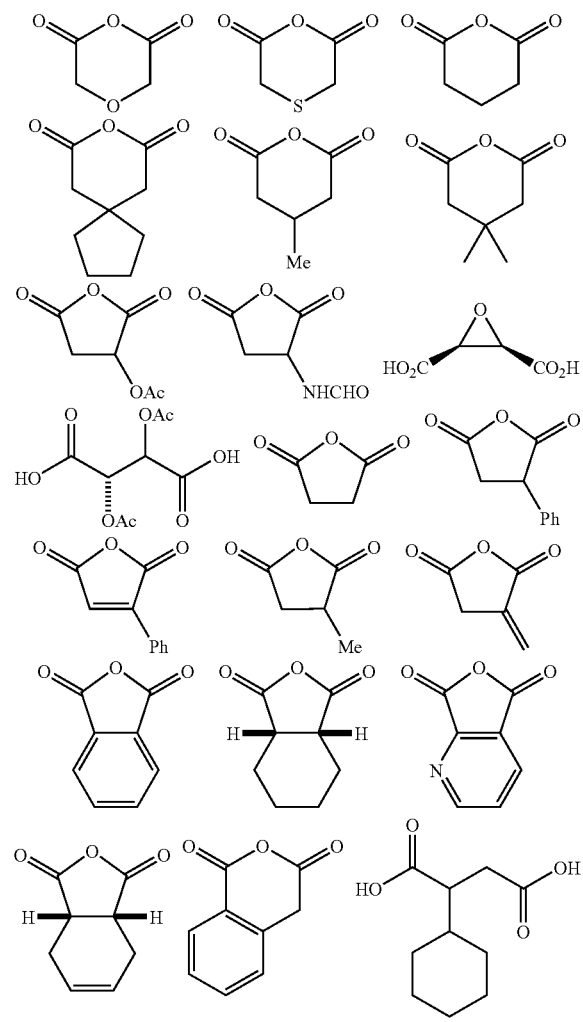

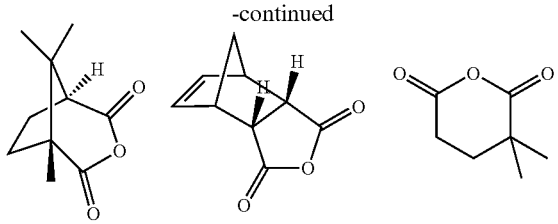

R was H or Me. X and the aromatic nucleus of Sector A were derived from the following aryl amines:

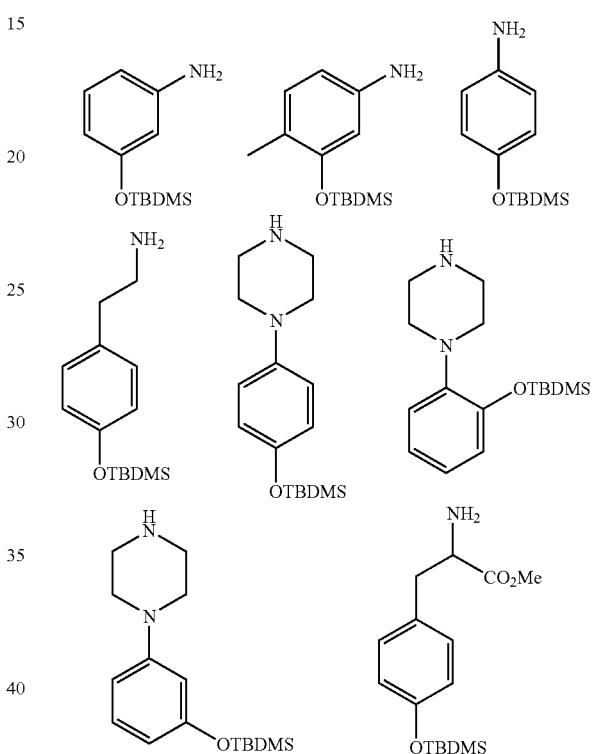

Members of this combinatorial library were synthesized as shown below:

Example 10A

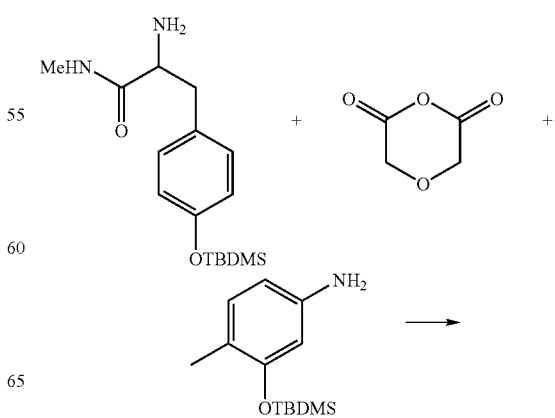

-continued
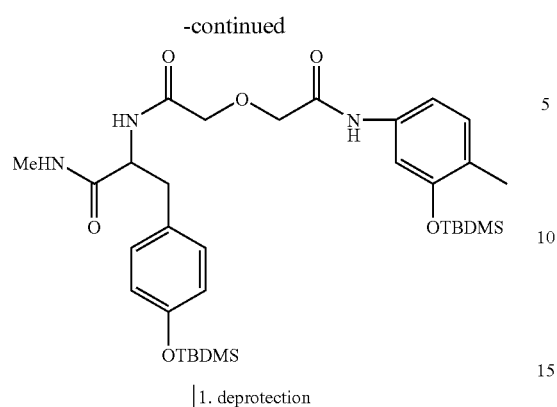
1. deprotection
2. sulfation
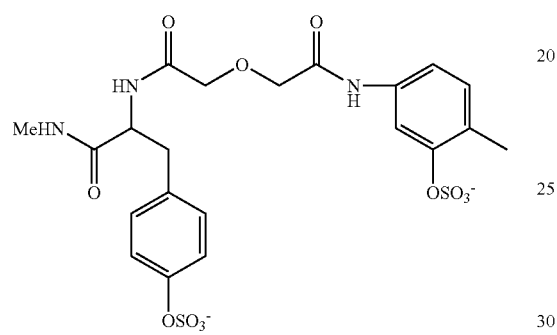
Example 10B
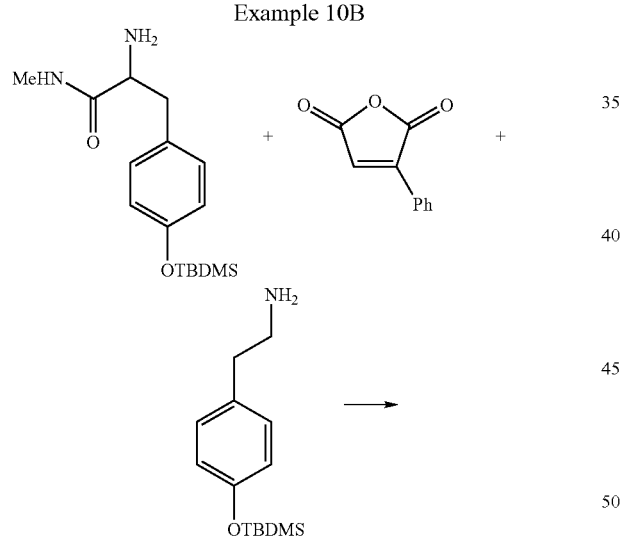
1. deprotection
2. sulfation
-continued
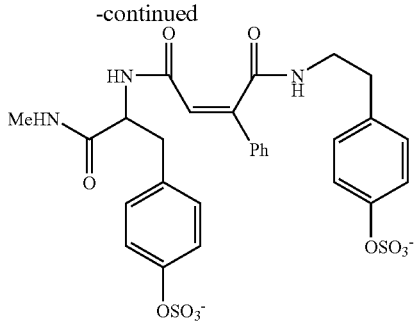
Example 10C
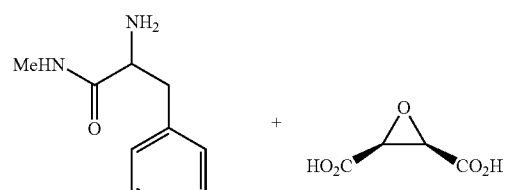
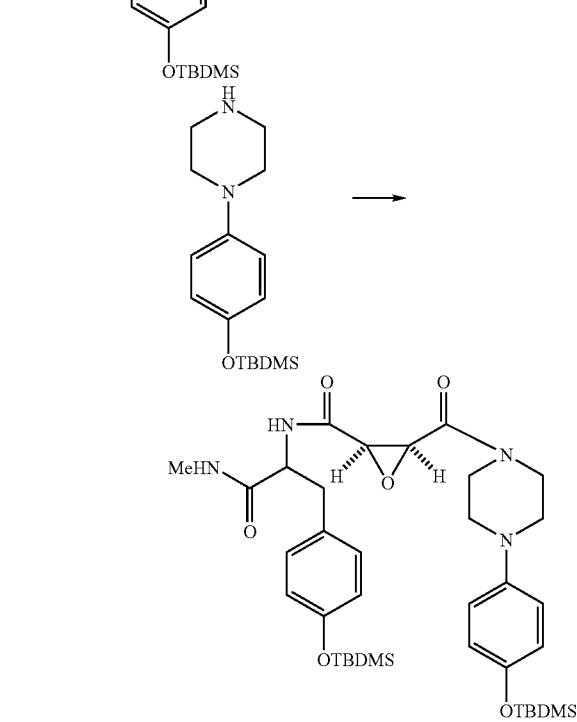
1. deprotection
2. sulfation
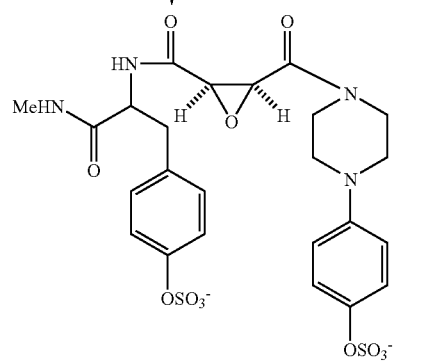

The general synthetic scheme for this combinatorial library is depicted below:
Synthetic scheme for synthesis of Template 3 compounds
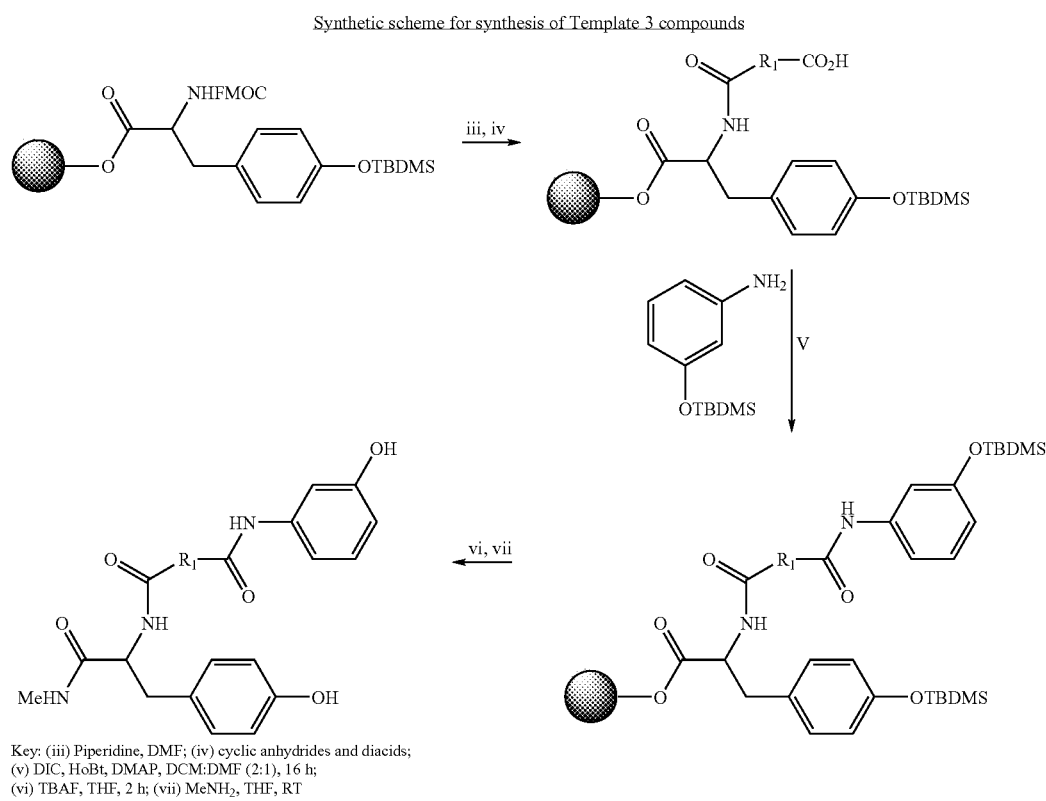
Key: (iii) Piperidine, DMF; (iv) cyclic anhydrides and diacids;
(v) DIC, HoBt, DMAP, DCM:DMF (2:1), 16 h;
(vi) TBAF, THF, 2 h; (vii) MeNH₂, THF, RT
Additional examples of compounds produced in this combinatorial library are shown below.
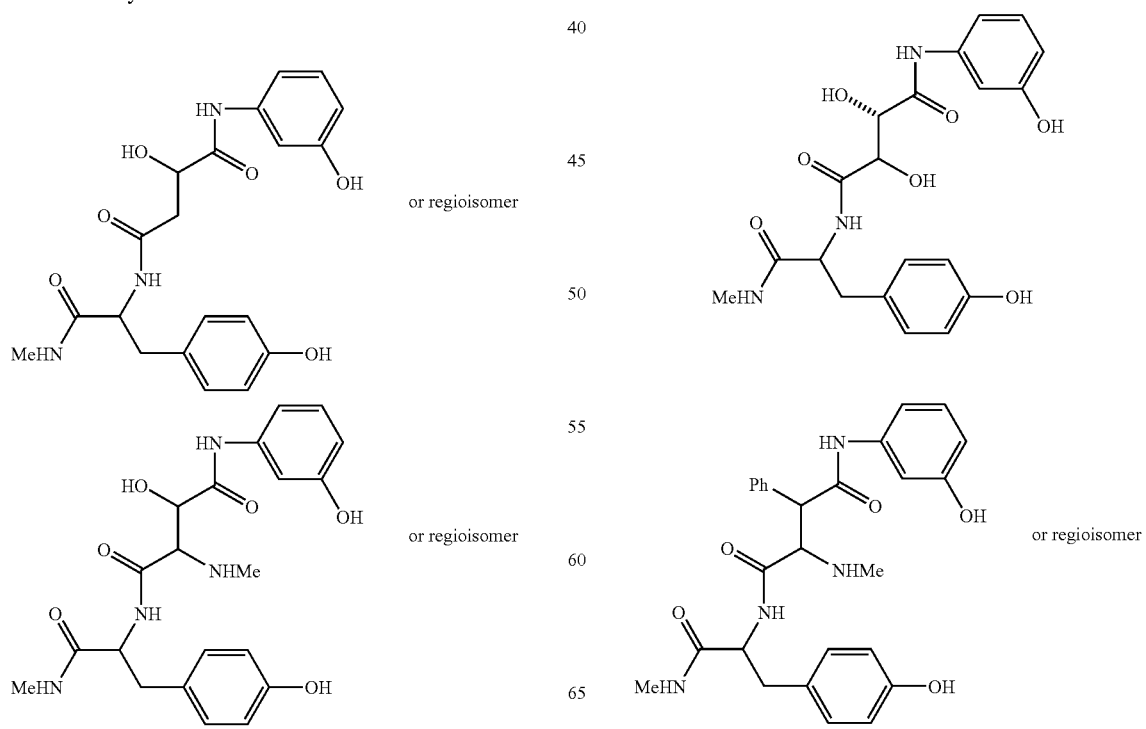

-continued

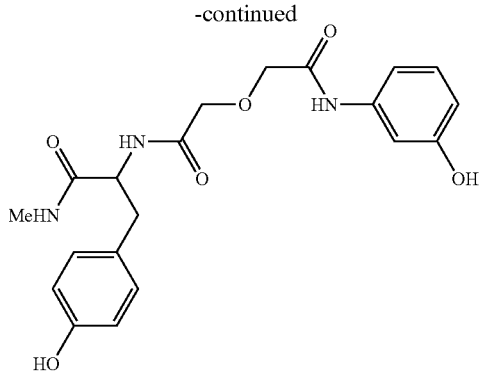

Selected members of this combinatorial library that were synthesized are listed in Tables 3 and 4 below:

TABLE 3

Mesylates according to Template 3:

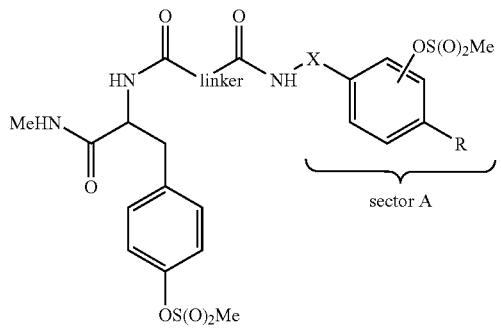

| Cmpd | R1 | R2 |
|---|---|---|
| 1 | SUCCINIC ANHYDRIDE | TYRAMINE |
| 2 | SUCCINIC ANHYDRIDE | L-TYROSINE METHYL ESTER |
| 3 | SUCCINIC ANHYDRIDE | N-(2-HYDROXYPHENYL)PIPERAZINE |
| 4 | SUCCINIC ANHYDRIDE | 1-(3-HYDROXYPHENYL)-PIPERAZINE |
| 5 | SUCCINIC ANHYDRIDE | 1-(4-HYDROXYPHENYL)-PIPERAZINE |
| 6 | SUCCINIC ANHYDRIDE | 3-AMINOPHENOL |
| 7 | SUCCINIC ANHYDRIDE | 5-AMINO-O-CRESOL |
| 8 | SUCCINIC ANHYDRIDE | 4-AMINOPHENOL |
| 9 | ITAONIC ANHYDRIDE | TYRAMINE |
| 10 | DIGLYCOLIC ANHYDRIDE | TYRAMINE |
| 11 | DIGLYCOLIC ANHYDRIDE | L-TYROSINE METHYL ESTER |
| 12 | DIGLYCOLIC ANHYDRIDE | N-(2-HYDROXYPHENYL)PIPERAZINE |
| 13 | DIGLYCOLIC ANHYDRIDE | 1-(3-HYDROXYPHENYL)-PIPERAZINE |
| 14 | DIGLYCOLIC ANHYDRIDE | 1-(4-HYDROXYPHENYL)-PIPERAZINE |
| 15 | DDIGLYCOLIC ANHYDRIDE | 3-AMINOPHENOL |
| 16 | DIGLYCOLIC ANHYDRIDE | 5-AMINO-O-CRESOL |
| 17 | DIGLYCOLIC ANHYDRIDE | 4-AMINOPHENOL |
| 18 | 3,3-TETRAMETHYLENEGLUTARIC ANHYDRIDE | TYRAMINE |
| 19 | 3,3-TETRAMETHYLENEGLUTARIC ANHYDRIDE | L-TYROSINE METHYL ESTER |
| 20 | 3,3-TETRAMETHYLENEGLUTARIC ANHYDRIDE | N-(2-HYDROXYPHENYL)PIPERAZINE |
| 21 | 3,3-TETRAMETHYLENEGLUTARIC ANHYDRIDE | 1-(3-HYDROXYPHENYL)-PIPERAZINE |
| 22 | 3,3-TETRAMETHYLENEGLUTARIC ANHYDRIDE | 1-(4-HYDROXYPHENYL)-PIPERAZINE |
| 23 | 3,3-TETRAMETHYLENEGLUTARIC ANHYDRIDE | 3-AMINOPHENOL |
| 24 | 3,3-TETRAMETHYLENEGLUTARIC ANHYDRIDE | 5-AMINO-O-CRESOL |
| 25 | 3,3-TETRAMETHYLENEGLUTARIC ANHYDRIDE | 4-AMINOPHENOL |
| 26 | PHENYLSUCCINIC ANHYDRIDE | TYRAMINE |
| 27 | PHENYLSUCCINIC ANHYDRIDE | L-TYROSINE METHYL ESTER |

TABLE 3-continued

Mesylates according to Template 3:

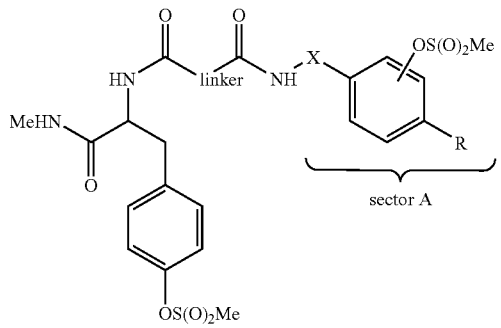

sector A

| Cmpd | R1 | R2 |
|---|---|---|
| 28 | PHENYLSUCCINIC ANHYDRIDE | N-(2-HYDROXYPHENYL)PIPERAZINE |
| 29 | PHENYLSUCCINIC ANHYDRIDE | 1-(3-HYDROXYPHENYL)-PIPERAZINE |
| 30 | PHENYLSUCCINIC ANHYDRIDE | 1-(4-HYDROXYPHENYL)-PIPERAZINE |
| 31 | PHENYLSUCCINIC ANHYDRIDE | 3-AMINOPHENOL |
| 32 | PHENYLSUCCINIC ANHYDRIDE | 5-AMINO-O-CRESOL |
| 33 | PHENYLSUCCINIC ANHYDRIDE | 4-AMINOPHENOL |
| 34 | GLUTARIC ANHYDRIDE | TYRAMINE |
| 35 | GLUTARIC ANHYDRIDE | N-(2-HYDROXYPHENYL)PIPERAZINE |
| 36 | GLUTARIC ANHYDRIDE | 1-(3-HYDROXYPHENYL)-PIPERAZINE |
| 37 | GLUTARIC ANHYDRDIE | 1-(4-HYDROXYPHENYL)-PIPERAZINE |
| 38 | GLUTARIC ANHYDRIDE | 3-AMINOPHENOL |
| 39 | GLUTARIC ANHYDRIDE | 5-AMINO-O-CRESOL |
| 40 | GLUTARIC ANHYDRIDE | 4-AMINOPHENOL |
| 41 | METHYL SUCCINIC ANHYDRIDE | TYRAMINE |
| 42 | METHYL SUCCINIC ANHYDRIDE | L-TYROSINE METHYL ESTER |
| 43 | METHYL SUCCINIC ANHYDRIDE | N-(2-HYDROXYPHENYL)PIPERAZINE |
| 44 | METHYL SUCCINIC ANHYDRIDE | 1-(3-HYDROXYPHENYL)-PIPERAZINE |
| 45 | METHYL SUCCINIC ANHYDRIDE | 1-(4-HYDROXYPHENYL)-PIPERAZINE |
| 46 | METHYL SUCCINIC ANHYDRIDE | 3-AMINOPHENOL |
| 47 | METHYL SUCCINIC ANHYDRIDE | 5-AMINO-O-CRESOL |
| 48 | METHYL SUCCINIC ANHYDRIDE | 4-AMINOPHENOL |
| 49 | (S)-(−)-2-FORMANAMIDOSUCCINIC ANHYDRIDE | N-(2-HYDROXYPHENYL)PIPERAZINE |
| 50 | (S)-(−)-2-FORMAMIDOSUCCINIC ANHYDRIDE | 1-(3-HYDROXYPHENYL)-PIPERAZINE |
| 51 | (S)-(−)-2-FORMAMIDOSUCCINIC ANHYDRIDE | 1-(4-HYDROXYPHENYL)-PIPERAZINE |
| 52 | (S)-(−)-2-FORMAMIDOSUCCINIC ANHYDRIDE | 3-AMINOPHENOL |
| 53 | (S)-(−)-O-ACETYLMALIC ANHYDRIDE | TYRAMINE |
| 54 | (S)-(−)-2-FORMAMIDOSUCCINIC ANHYDRIDE | 5-AMINO-O-CRESOL |
| 55 | (S)-(−)-O-ACETYLMALIC ANHYDRIDE | N-(2-HYDROXYPHENYL)PIPERAZINE |
| 56 | (S)-(−)-O-ACETYLMALIC ANHYDRIDE | 1-(4-HYDROXYPHENYL)-PIPERAZINE |
| 57 | (S)-(−)-O-ACETYLMALIC ANHYDRIDE | 3-AMINOPHENOL |
| 58 | (S)-(−)-O-ACETYLMALIC ANHYDRIDE | 5-AMINO-O-CRESOL |
| 59 | (S)-(−)-O-ACETYLMALIC ANHYDRIDE | 4-AMINOPHENOL |
| 60 | THIODIGLYCOLIC ANHYDRIDE | TYRAMINE |
| 61 | THIODIGLYCOLIC ANHYDRIDE | L-TYROSINE METHYL ESTER |
| 62 | THIODIGLYCOLIC ANHYDRIDE | N-(2-HYDROXYPHENYL)PIPERAZINE |
| 63 | THIODIGLYCOLIC ANHYDRIDE | 1-(3-HYDROXYPHENYL)-PIPERAZINE |
| 64 | THIODIGLYCOLIC ANHYDRIDE | 1-(4-HYDROXYPHENYL)-PIPERAZINE |
| 65 | THIODIGLYCOLIC ANHYDRIDE | 3-AMINOPHENOL |
| 66 | THIODIGLYCOLIC ANHYDRIDE | 5-AMINO-O-CRESOL |
| 67 | THIODIGLYCOLIC ANHYDRIDE | 4-AMINOPHENOL |
| 68 | 3-METHYLGLUTARIC ANHYDRIDE | TYRAMINE |

TABLE 3-continued

Mesylates according to Template 3:

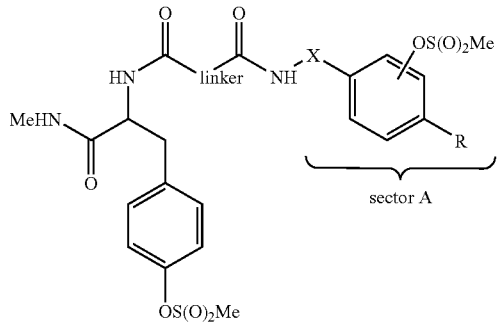

sector A

| Cmpd | R1 | R2 |
|---|---|---|
| 69 | 3-METHYLGLUTARIC ANHYDRIDE | L-TYROSINE METHYL ESTER |
| 70 | 3-METHYLGLUTARIC ANHYDRIDE | N-(2-HYDROXYPHENYL)PIPERAZINE |
| 71 | 3-METHYLGLUTARIC ANHYDRIDE | 1-(3-HYDROXYPHENYL)-PIPERAZINE |
| 72 | 3-METHYLGLUTARIC ANHYDRIDE | 1-(4-HYDROXYPHENYL)-PIPERAZINE |
| 73 | 3-METHYLGLUTARIC ANHYDRIDE | 3-AMINOPHENOL |
| 74 | 3-METHYLGLUTARIC ANHYDRIDE | 5-AMINO-O-CRESOL |
| 75 | 3-METHYLGLUTARIC ANHYDRIDE | 4-AMINOPHENOL |
| 76 | 3,3-DIMETHYLGLUTARIC ANHYDRIDE | L-TYROSINE METHYL ESTER |
| 77 | 3,3-DIMETHYLGLUTARIC ANHYDRIDE | N-(2-HYDROXYPHENYL)PIPERAZINE |
| 78 | 3,3-DIMETHYLGLUTARIC ANHYDRIDE | 1-(3-HYDROXYPHENYL)-PIPERAZINE |
| 79 | 3,3-DIMETHYLGLUTARIC ANHYDRIDE | 3-AMINOPHENOL |
| 80 | 3,3-DIMETHYLGLUTARIC ANHYDRIDE | 4-AMINOPHENOL |
| 81 | 3,3-DIMETHYLGLUTARIC ANHYDRIDE | 5-AMINO-O-CRESOL |
| 82 | 3,3-DIMETHYLGLUTARIC ANHYDRIDE | 1-(4-HYDROXYPHENYL)-PIPERAZINE |
| 83 | CIS-EPOXYSUCCINIC ACID | TYRAMINE |
| 84 | CIS-EPOXYSUCCINIC ACID | L-TYROSINE METHYL ESTER |
| 85 | CIS-EPOXYSUCCINIC ACID | N-(2-HYDROXYPHENYL)PIPERAZINE |
| 86 | CIS-EPOXYSUCCINIC ACID | 1-(3-HYDROXYPHENYL)-PIPERAZINE |
| 87 | CIS-EPOXYSUCCINIC ACID | 1-(4-HYDROXYPHENYL)-PIPERAZINE |
| 88 | CIS-EPOXYSUCCINIC ACID | 3-AMINOPHENOL |
| 89 | CIS-EPOXYSUCCINIC ACID | 5-AMINO-O-CRESOL |
| 90 | CIS-EPOXYSUCCINIC ACID | 4-AMINOPHENOL |
| 91 | PHENYLMALEIC ANHYDRIDE | TYRAMINE |
| 92 | PHENYLMALEIC ANHYDRIDE | L-TYROSINE METHYL ESTER |
| 93 | PHENYLMALEIC ANHYDRIDE | N-(2-HYDROXYPHENYL)PIPERAZINE |
| 94 | PHENYLMALEIC ANHYDRIDE | 1-(3-HYDROXYPHENYL)-PIPERAZINE |
| 95 | PHENYLMALEIC ANHYDRIDE | 1-(4-HYDROXYPHENYL)-PIPERAZINE |
| 96 | PHTHALIC ANHYDRIDE | TYRAMINE |
| 97 | PHTHALIC ANHYDRIDE | L-TYROSINE METHYL ESTER |
| 98 | PHTHALIC ANHYDRIDE | N-(2-HYDROXYPHENYL)PIPERAZINE |
| 99 | PHTHALIC ANHYDRIDE | 1-(3-HYDROXYPHENYL)-PIPERAZINE |
| 100 | PHTHALIC ANHYDRIDE | 1-(4-HYDROXYPHENYL)-PIPERAZINE |
| 101 | 2,3-PYRIDINEDICARBOXYLIC ANHYDRIDE | TYRAMINE |
| 102 | 2,3-PYRIDINEDICARBOXYLIC ANHYDRIDE | L-TYROSINE METHYL ESTER |
| 103 | 2,3-PYRIDINEDICARBOXYLIC ANHYDRIDE | N-(2-HYDROXYPHENYL)PIPERAZINE |
| 104 | 2,3-PYRIDINEDICARBOXYLIC ANHYDRIDE | 1-(3-HYDROXYPHENYL)-PIPERAZINE |
| 105 | 2,3-PYRIDINEDICARBOXYLIC ANHYDRIDE | 1-(4-HYDROXYPHENYL)-PIPERAZINE |
| 106 | CIS-1,2,3,6-TETRAHYDROPHTHALIC ANHYDRIDE | TYRAMINE |

TABLE 3-continued

Mesylates according to Template 3:

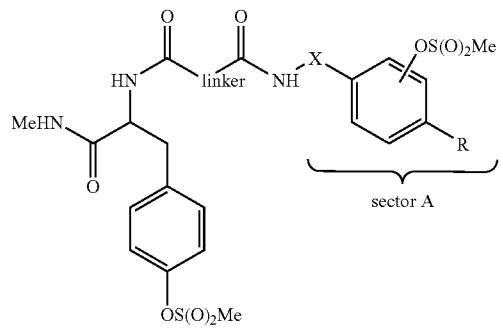

sector A

| Cmpd | R1 | R2 |
| --- | --- | --- |
| 107 | CIS-1,2,3,6-TETRAHYDROPHTHALIC ANHYDRIDE | L-TYROSINE METHYL ESTER |
| 108 | CIS-1,2,3,6-TETRAHYDROPHTHALIC ANHYDRIDE | N-(2-HYDROXYPHENYL)PIPERAZINE |
| 109 | CIS-1,2,3,6-TETRAHYDROPHTHALIC ANHYDRIDE | 1-(3-HYDROXYPHENYL)-PIPERAZINE |
| 110 | CIS-1,2,3,6-TETRAHYDROPHTHALIC ANHYDRIDE | 1-(4-HYDROXYPHENYL)-PIPERAZINE |
| 111 | CIS-1,2-CYCLOHEXANEDICARBOXYLIC ANHYDRIDE | TYRAMINE |
| 112 | CIS-1,2-CYCLOHEXANEDICARBOXYLIC ANHYDRIDE | L-TYROSINE METHYL ESTER |
| 113 | CIS-1,2-CYCLOHEXANEDICARBOXYLIC ANHYDRIDE | N-(2-HYDROXYPHENYL)PIPERAZINE |
| 114 | CIS-1,2-CYCLOHEXANEDICARBOXYLIC ANHYDRIDE | 1-(3-HYDROXYPHENYL)-PIPERAZINE |
| 115 | CIS-1,2-CYCLOHEXANEDICARBOXYLIC ANHYDRIDE | 1-(4-HYDROXYPHENYL)-PIPERAZINE |
| 116 | DL-CAMPHORIC ANHYDRIDE | TYRAMINE |
| 117 | DL-CAMPHORIC ANHYDRIDE | L-TYROSINE METHYL ESTER |
| 118 | CIS-5-NORBORMEME-2,3-DICARBOXYLIC ANHYDRIDE | TYRAMINE |
| 119 | CIS-5-NORBORNENE-2,3-DICARBOXYLIC ANHYDRIDE | L-TYROSINE METHYL ESTER |
| 120 | 2,2-DIMETHYLGLUTARIC ANHYDRIDE | TYRAMINE |
| 121 | 2,2-DIMETHYLGLUTARIC ANHYDRIDE | L-TYROSINE METHYL ESTER |
| 122 | 2,2-DIMETHYLGLUTARIC ANHYDRIDE | N-(2-HYDROXYPHENYL)PIPERAZINE |
| 123 | 2,2-DIMETHYLGLUTARIC ANHYDRIDE | 1-(3-HYDROXYPHENYL)-PIPERAZINE |
| 124 | 2,2-DIMETHYLGLUTARIC ANHYDRIDE | 1-(4-HYDROXYPHENYL)-PIPERAZINE |
| 125 | HOMOPHTHALIC ANHYDRIDE | TYRAMINE |
| 126 | HOMOPHTHALIC ANHYDRIDE | L-TYROSINE METHYL ESTER |
| 127 | HOMOPHTHALIC ANHYDRIDE | N-(2-HYDROXYPHENYL)PIPERAZINE |
| 128 | HOMOPHTHALIC ANHYDRIDE | 1-(3-HYDROXYPHENYL)-PIPERAZINE |
| 129 | HOMOPHTHALIC ANHYDRIDE | 1-(4-HYDROXYPHENYL)-PIPERAZINE |

TABLE 4

Triflates according to Template 3:

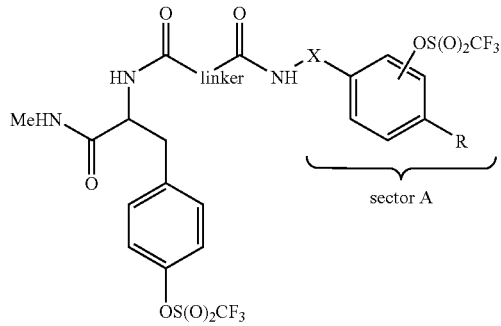

| Cmpd | Linker derived from | Sector A derived from |
|---|---|---|
| 1 | SUCCINIC ANHYDRIDE | 1-(3-HYDROXYPHENYL)-PIPERAZINE |
| 2 | SUCCINIC ANHYDRIDE | 3-AMINOPHENOL |
| 3 | SUCCINIC ANHYDRIDE | 5-AMINO-O-CRESOL |
| 4 | DIGLYCOLIC ANHYDRIDE | L-TYROSINE METHYL ESTER |
| 5 | DIGLYCOLIC ANHYDRIDE | 3-AMINOPHENOL |
| 6 | 3,3-TETRAMETHYLENEGLUTARIC ANHYDRIDE | 3-AMINOPHENOL |
| 7 | 3,3-TETRAMETHYLENEGLUTARIC ANHYDRIDE | 5-AMINO-O-CRESOL |
| 8 | 3,3-TETRAMETHYLENEGLUTARIC ANHYDRIDE | 4-AMINOPHENOL |
| 9 | PHENYLSUCCINIC ANHYDRIDE | L-TYROSINE METHYL ESTER |
| 10 | PHENYLSUCCINIC ANHYDRIDE | N-(2-HYDROXYPHENYL)PIPERAZINE |
| 11 | PHENYLSUCCINIC ANHYDRIDE | 3-AMINOPHENOL |
| 12 | PHENYLSUCCINIC ANHYDRIDE | 5-AMINO-O-CRESOL |
| 13 | PHENYLSUCCINIC ANHYDRIDE | 4-AMINOPHENOL |
| 14 | GLUTARIC ANHYDRIDE | 5-AMINO-O-CRESOL |
| 15 | METHYL SUCCINIC ANHYDRIDE | L-TYROSINE METHYL ESTER |
| 16 | METHYL SUCCINIC ANHYDRIDE | N-(2-HYDROXYPHENYL)-PIPERAZINE |
| 17 | METHYL SUCCINIC ANHYDRIDE | 1-(3-HYDROXYPHENYL)-PIPERAZINE |
| 18 | METHYL SUCCINIC ANHYDRIDE | 1-(4-HYDROXYPHENYL)-PIPERAZINE |
| 19 | METHYL SUCCINIC ANHYDRIDE | 3-AMINOPHENOL |
| 20 | METHYL SUCCINIC ANHYDRIDE | 5-AMINO-O-CRESOL |
| 21 | METHYL SUCCINIC ANHYDRIDE | 4-AMINOPHENOL |
| 22 | (S)-(−)-O-ACETYLAMLIC ANHYDRIDE | N-(2-HYDROXYPHENYL)PIPERAZINE |
| 23 | (S)-(−)-O-ACETYLMALIC ANHYDRIDE | 1-(3-HYDROXYPHENYL)-PIPERAZINE |
| 24 | (S)-(−)-O-ACETYLMALIC ANHYDRIDE | 5-AMINO-O-CRESOL |
| 25 | (S)-(−)-O-ACETYLMALIC ANHYDRIDE | 4-AMINOPHENOL |
| 26 | THIODIGLYCOLIC ANHYDRIDE | N-(2-HYDROXYPHENYL)PIPERAZINE |
| 27 | THIODIGLYCOLIC ANHYDRIDE | 1-(3-HYDROXYPHENYL)-PIPERAZINE |
| 28 | THIODIGLYCOLIC ANHYDRIDE | 1-(4-HYDROXYPHENYL)-PIPERAZINE |
| 29 | THIODIGLYCOLIC ANHYDRIDE | 3-AMINOPHENOL |
| 30 | THIODIGLYCOLIC ANHYDRIDE | 5-AMINO-O-CRESOL |
| 31 | THIODIGLYCOLIC ANHYDRIDE | 4-AMINOPHENOL |
| 32 | 3-METHYLGLUTARIC ANHYDRIDE | 3-AMINOPHENOL |
| 33 | 3,3-DIMETHYLGLUTARIC ANHYDRIDE | N-(2-HYDROXYPHENYL)PIPERAZINE |
| 34 | 3,3-DIMETHYLGLUTARIC ANHYDRIDE | 3-AMINOPHENOL |
| 35 | CIS-EPOXYSUCCINIC ACID | 5-AMINO-O-CRESOL |
| 36 | CIS-1,2,3,6-TETRAHYDROPHTHALIC ANHYDRIDE | 1-(3-HYDROXYPHENYL)-PIPERAZINE |
| 37 | CIS-1,2,3,6-TETRAHYDROPHTHALIC ANHYDRIDE | 1-(4-HYDROXYPHENYL)-PIPERAZINE |
| 38 | HOMOPHTHALIC ANHYDRIDE | 1-(3-HYDROXYPHENYL)-PIPERAZINE |
| 39 | HOMOPHTHALIC ANHYDRIDE | 1-(4-HYDROXYPHENYL)-PIPERAZINE |

Example 11
Synthesis of a Bis-Sulfonic Acid
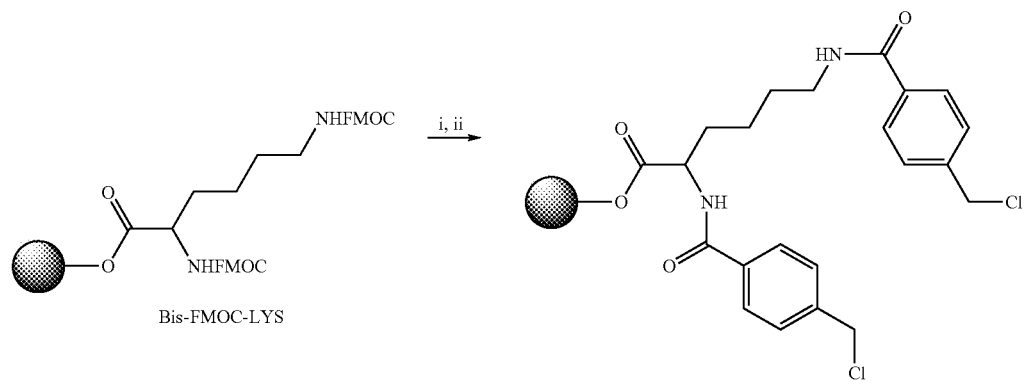
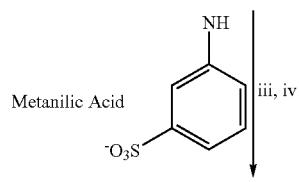
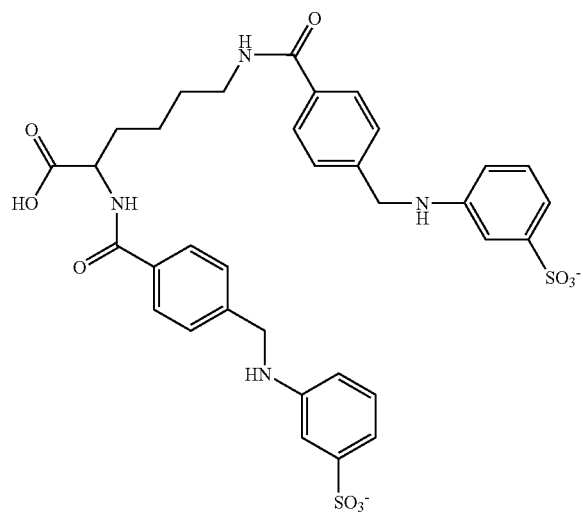
Key: (i) Piperidine/DMF (1:1); (ii) 4-chloromethylbenzoic acid, DIC;
(iii) metanilic acid, DMSO, 55 deg. C, base; (iv) 20% TFA/DCM

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound represented by 1:

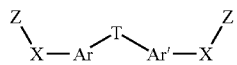

wherein
X represents independently for each occurrence a bond, O, S, or NR';
Z represents independently for each occurrence H, acyl, trialkylsilyl, alkylsulfonyl, fluoroalkylsulfonyl, arylsulfonyl, or $S(O)_2OH$;
Ar and Ar' are optionally substituted naphthyl or optionally substituted phenyl, wherein one of Ar and Ar' is optionally substituted naphthyl and one of Ar and Ar' is optionally substituted phenyl;
T represents a covalent tether connecting Ar and Ar', wherein said covalent tether comprises two or more moieties selected from the following: amide, ether, amine or ester moiety;
R represents independently for each occurrence H, alkyl, aryl, or aralkyl;
R' represents independently for each occurrence H, alkyl, alkenyl, aryl, aralkyl, formyl, acyl, sulfonyl, or —$(CH_2)_m$—$R_{80}$;
$R_{80}$ represents independently for each occurrence aryl, cycloalkyl, cycloalkenyl, or heterocyclyl; and
m is an integer in the range 0 to 8 inclusive.

2. The compound of claim 1, wherein X represents independently for each occurrence a bond or O.

3. The compound of claim 1, wherein X represents O.

4. The compound of claim 1, wherein Z represents independently for each occurrence H, alkylsulfonyl, fluoroalkylsulfonyl, arylsulfonyl, or $S(O)_2OH$.

5. The compound of claim 1, wherein Z represents independently for each occurrence H, methylsulfonyl, trifluoromethylsulfonyl, or $S(O)_2OH$.

6. The compound of claim 1, wherein X represents O; and Z represents independently for each occurrence H, alkylsulfonyl, fluoroalkylsulfonyl, arylsulfonyl, or $S(O)_2OH$.

7. The compound of claim 1, wherein X represents O; and Z represents independently for each occurrence H, alkylsulfonyl, fluoroalkylsulfonyl, arylsulfonyl, or $S(O)_2OH$.

8. The compound of claim 1, wherein X represents O; and Z represents independently for each occurrence H, methylsulfonyl, trifluoromethylsulfonyl, or $S(O)_2OH$.

9. The compound of claim 1, wherein T represents —C(O)NR—Q—NRC(O)—; Q is —$(CH_2)_n$— or heterocyclyl; and n is an integer selected from the range 2 to 10 inclusive.

10. The compound of claim 1, wherein T represents —$(CH_2)$—NR—Q—O—; and Q represents alkyl, cycloalkyl, or heterocyclyl.

11. The compound of claim 1, wherein T represents —$(CH_2)$—NR—Q—O—C(O)— or —$(CH_2)$—NR—Q—O—C(O)—(CH=CH)—; and Q represents alkyl, cycloalkyl, or heterocyclyl.

12. The compound of claim 1, wherein T represents —$(CH_2)$—NR—Q—; and Q is a bond, alkyl, or heterocyclyl.

13. The compound of claim 1, wherein T represents —$CH_2CH(C(O)NHMe)$—NRC(O)—Q—C(O)NR—G—; Q is alkyl, cycloalkyl, cycloalkenyl, heterocyclyl, alkenyl, aryl, heteroaryl, aralkyl, alkyl-O-alkyl, or alkyl-S-alkyl; and G is a bond, alkyl, or heterocyclyl.

14. A composition, comprising the compound of claim 1 and a pharmaceutically acceptable carrier.

* * * * *